USO10431342B2

(12) United States Patent
Kovatchev et al.

(10) Patent No.: US 10,431,342 B2
(45) Date of Patent: Oct. 1, 2019

(54) TRACKING THE PROBABILITY FOR IMMINENT HYPOGLYCEMIA IN DIABETES FROM SELF-MONITORING BLOOD GLUCOSE (SMBG) DATA

(75) Inventors: Boris P. Kovatchev, Charlottesville, VA (US); Marc D. Breton, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1286 days.

(21) Appl. No.: 13/394,091
(22) PCT Filed: Sep. 2, 2010
(86) PCT No.: PCT/US2010/047711
§ 371 (c)(1),
(2), (4) Date: Mar. 22, 2012
(87) PCT Pub. No.: WO2011/028925
PCT Pub. Date: Mar. 10, 2011

(65) Prior Publication Data
US 2012/0191361 A1 Jul. 26, 2012

Related U.S. Application Data

(60) Provisional application No. 61/239,291, filed on Sep. 2, 2009.

(51) Int. Cl.
*G01N 33/48* (2006.01)
*G16H 50/50* (2018.01)
(Continued)

(52) U.S. Cl.
CPC ............ *G16H 50/50* (2018.01); *G06F 19/00* (2013.01); *A61B 5/0002* (2013.01); *G01N 2800/042* (2013.01)

(58) Field of Classification Search
CPC . A61B 5/14532; A61B 5/7275; A61B 5/7264; A61B 5/00; G06F 19/345;
(Continued)

(56) References Cited

U.S. PATENT DOCUMENTS 5,971,922 A 10/1999 Arita et al.
6,923,763 B1 8/2005 Kovatchev et al.
(Continued)

FOREIGN PATENT DOCUMENTS

WO 2009009528 A1 1/2009
WO 2010/114929 A1 10/2010

OTHER PUBLICATIONS

Andreaseen et al., "A Probabilistic Approach to Glucose Prediction and Insulin Dose Adjustment: Description of Metabolic Model and Pilot Evaluation Study," Computer Methods and Programs in Biomedicine [online], Jan. 1994, vol. 41, No. 3-4, pp. 153-165.
(Continued)

*Primary Examiner* — Larry D Riggs, II
(74) *Attorney, Agent, or Firm* — Vorys, Sater, Seymour and Pease LLP; Vincent M DeLuca; Robert J Decker

(57) ABSTRACT

A method, system and related computer program product for tracking the probability of hypoglycemia from routine self-monitoring of blood glucose (SMBG) data in patients with diabetes. A specific bivariate probability distribution of low BG events based jointly on the Low BG Index (LBGI) and the Average Daily Risk Range (ADRR) is used to predict hypoglycemia probability of occurrence from inputted SMBG data. The SMBG data is retrieved from a series of SMBG data of a patient available from the patient's glucose meter and allows tracking of the probability for future hypoglycemia over a predetermined duration, e.g., a 24 or 48 hour period. The tracking includes presentation of visual and/or numerical output, as we construction of hypoglycemia risk trajectories that would enable warning messages for crossing of predefined thresholds, such as 50% likelihood for upcoming hypoglycemia below 50 mg/dl.

43 Claims, 7 Drawing Sheets

(51) Int. Cl.
*G06F 19/00* (2018.01)
*A61B 5/00* (2006.01)

(58) Field of Classification Search
CPC .............. G06F 19/3487; G06F 19/322; G06F 19/3431; A61M 2230/201; A61M 5/1723
See application file for complete search history.

(56) References Cited

U.S. PATENT DOCUMENTS

| | | |
|---|---|---|
| 2005/0192494 A1 | 9/2005 | Ginsberg |
| 2005/0214892 A1 | 9/2005 | Kovatchev et al. |
| 2006/0094947 A1 | 5/2006 | Kovatchev et al. |
| 2006/0167365 A1 | 7/2006 | Bharmi |
| 2006/0247685 A1 | 11/2006 | Bharmi |
| 2007/0232878 A1 | 10/2007 | Kovatchev |
| 2008/0009684 A1 | 1/2008 | Corsetti et al. |
| 2008/0021666 A1 | 1/2008 | Goode, Jr. et al. |
| 2008/0154513 A1 | 6/2008 | Kovatchev et al. |
| 2008/0234992 A1 | 9/2008 | Ray et al. |
| 2009/0171589 A1 | 7/2009 | Kovatchev et al. |
| 2009/0299152 A1 | 12/2009 | Taub et al. |

OTHER PUBLICATIONS

McCall et al., "Reduced Daily Risk of Glycemic Variability: Comparison of Exenatide with Insuliini Glargine," Diabetes Technology & Therapeutics [online], May 21, 2009, vol. 11, No. 6, pp. 339-344.

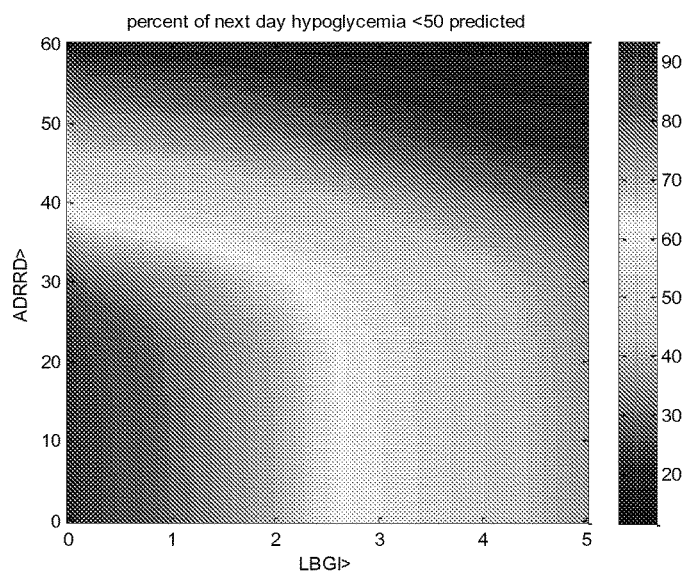
Figure 3A: Percent prediction announcements depending on ADRR and LBGI cutoff values (each point corresponds to a LBGI>α & ADRR>β)
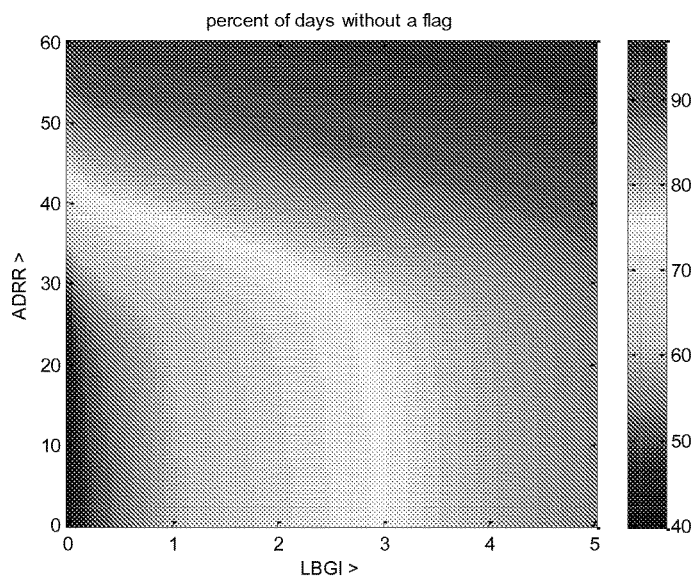
Figure 3B: Percent days without flags depending on ADRR and LBGI cutoff values (each point corresponds to a LBGI>α & ADRR>β)

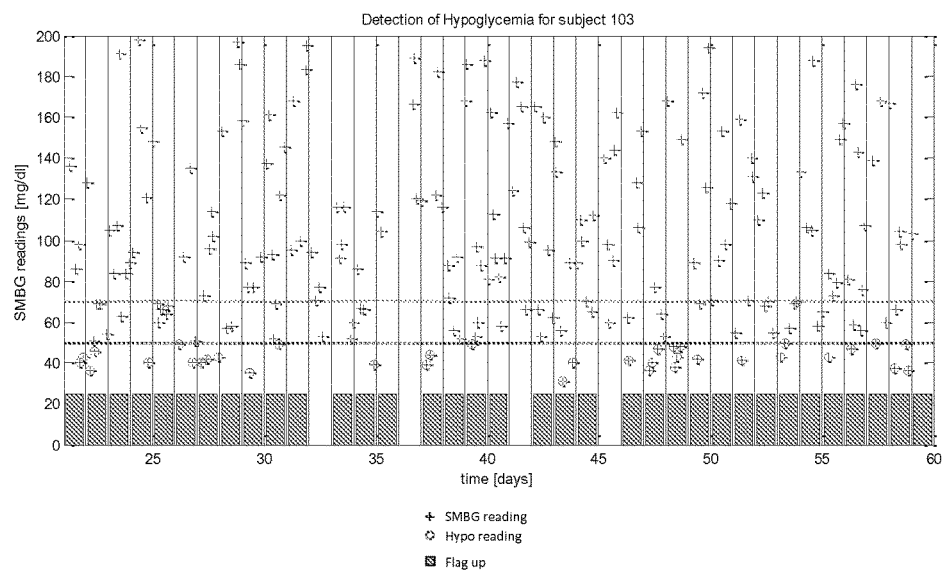
Figure 4A: Example of the action of the method tracking the risk for hypoglycemia in one subject who experienced frequent hypoglycemic episodes
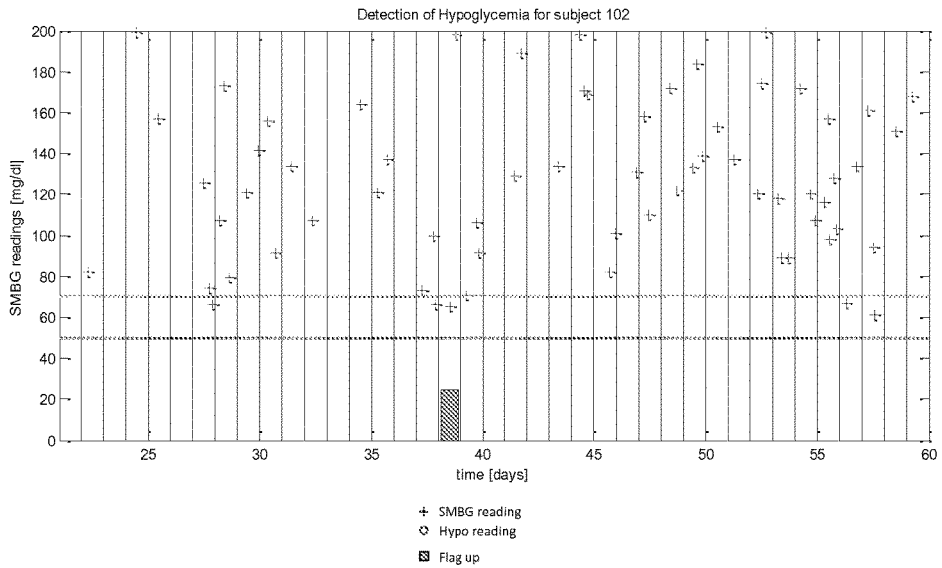
Figure 4B: Example of the action of the method tracking the risk for hypoglycemia in one subject who did not experience hypoglycemia

TRACKING THE PROBABILITY FOR IMMINENT HYPOGLYCEMIA IN DIABETES FROM SELF-MONITORING BLOOD GLUCOSE (SMBG) DATA

GOVERNMENT SUPPORT

Work described herein was supported by Federal Grant No. R01 DK51562, awarded by National Institutes of Health (NIH). The US Government has certain rights in the invention.

BACKGROUND OF THE INVENTION

B.1. Hypoglycemia in Diabetes

Hypoglycemia is common in Type 1 Diabetes Mellitus (T1DM) [24] and becomes more prevalent in Type 2 Diabetes Mellitus (T2DM) with treatment intensification [7]. Hypoglycemia-associated autonomic failure (HAAF) is well documented in T1DM [4] and is observed in intensively treated T2DM as well [22]. Even state-of-the-art therapies are imperfect and may trigger acute lowering of blood glucose (BG) levels, potentially leading to severe hypoglycemia (SH), defined as severe neuroglycopenia resulting in unconsciousness or stupor that precludes self-treatment [24]. SH may cause cognitive dysfunction, coma, or sudden death [6, 24]. Consequently, hypoglycemia has been identified as the primary barrier to optimal diabetes management [3].

B.2. Potential Predictors of Hypoglycemia

Glycosylated hemoglobin ($HbA_{1c}$) is the classic marker of glycemic status, introduced 23 years ago [1], linked to diabetes complications, and confirmed as the gold standard measure of average glycemic control in T1DM and T2DM, [20, 25, 27]. However, in addition to establishing $HbA_{1c}$, the Diabetes Control and Complications Trial (DCCT) concluded that: "$HbA_{1c}$ is not the most complete expression of the degree of glycemia. Other features of diabetic glucose control, which are not reflected by $HbA_{1c}$, may add to, or modify the risk of complications. For example, the risk of complications may be more highly dependent on the extent of postprandial glycemic excursions" [26]. Consequently, contemporary studies increasingly concentrate on the variability of BG fluctuations as an independent factor for diabetes complications [2]. The two most prominent manifestations of glycemic variability are hypoglycemia and postprandial glucose (PPG) elevation.

Standard Deviation and Other Variability Measures:

The traditional statistical calculation of BG variability includes computing the standard deviation (SD) of BG readings as well as several other measures: (i) The M-value introduced in 1965 [21]; (ii) MAGE—Mean Amplitude of Glucose Excursions—introduced in 1970 [23], and (iii) the Lability Index (LI)—a recently developed measure of hypoglycemia and glycemic lability [19]. Most of these measures (except the LI) have a relatively weak association with hypoglycemia and an inherent bias towards hyperglycemia, which is reflected by the historically poor prediction of SH [24]. In previous studies, we have found that the basis for that poor prediction appeared to be mathematical, rather than clinical: it lies in the fact that the BG measurement scale is asymmetric and substantially skewed towards hyperglycemia [13]. Thus, clinical conclusions based on numerical methods, will be less accurate for the constricted hypoglycemic range and will be biased towards hyperglycemia.

B.3. Risk Analysis of BG Data

In order to correct the numerical problem created by the asymmetry of the BG scale we have introduced a mathematical transformation that symmetrizes the BG scale [13]. It is important to note that the analytical form of this transformation is based on accepted clinical assumptions, not on a particular data set, and has been fixed ten years ago [13], which makes the approach extendable to any data set. Based on this transformation, we have developed our theory of risk analysis of BG data [12, 15, 8] that defines a computational risk space that proved to be very suitable for quantifying the extent and frequency of glucose excursions. In essence, analysis in risk space entails converting first each BG reading into a risk value using two simple steps: (i) application of the symmetrization formula [13], and (ii) application of a quadratic risk function that assigns increasing weights to larger BG deviations towards hypoglycemia or hyperglycemia [18]. In brief, the BG measurement scale is numerically asymmetric—the hyperglycemic range (180 to 600 mg/dl) is much greater that the hypoglycemic range (20-70 mg/dl) and the euglycemic range (70-180 mg/dl) is not centered within the scale. We have corrected this asymmetry by introducing a transformation f(BG)—a continuous function defined on the BG range [20, 600] that has the general two-parameter analytical form [13]:

$$f(BG,\alpha,\beta)=[(\ln(BG))^\alpha-\beta], \alpha,\beta>0$$

and satisfies the assumptions:

$$f(600,\alpha,\beta)=-f(20,\alpha,\beta) \text{ and} \quad\quad\quad A1:$$

$$f(180,\alpha,\beta)=-f(70,\alpha,\beta). \quad\quad\quad A2:$$

By multiplying by a third parameter γ we fix the minimal and maximal values of the transformed BG range at $-\sqrt{10}$ and $\sqrt{10}$ respectively. When solved numerically under the restriction α>0, these equations give: α=1.084, β=5.381, γ=1.509. These parameters are sample-independent and have been fixed in 1997 [13].

After fixing the parameters off(BG) depending on the measurement scale that is being used, we define the quadratic function $r(BG)=10f(BG)^2$, which defines the BG Risk Space. The function r(BG) ranges from 0 to 100. Its minimum value is 0 and is achieved at BG=112.5 mg/dl, a safe euglycemic BG reading, while its maximum is reached at the extreme ends of the BG scale (20 mg/dl and 600 mg/dl). Thus, r(BG) can be interpreted as a measure of the risk associated with a certain BG level. The left branch of this parabola identifies the risk of hypoglycemia, while the right branch identifies the risk of hyperglycemia. These branches are identified by the formulas [18]:

$$rl(BG)=r(BG) \text{ if } f(BG)<0 \text{ and } 0 \text{ otherwise (left branch);} \quad\quad (1)$$

$$rh(BG)=r(BG) \text{ if } f(BG)>0 \text{ and } 0 \text{ otherwise (right branch).} \quad\quad (2)$$

The Low BG Index (LBGI): is based on the left branch of the BG Risk Function (BG) and accounts for the frequency and extent of hypoglycemia. The LBGI has been validated by multiple studies as an excellent predictor of future significant hypoglycemia [10, 11, 12, 14, 15]. The LBGI also provides means for classification of the subjects with regard to their long-term risk for hypoglycemia into: Minimal, Low, Moderate and High-risk groups, with LBGI of below 1.1, 1.1-2.5, 2.5-5.0, and above 5.0 respectively [15], and has been used for short term prediction of hypoglycemia as well [5, 9]. By definition, the LBGI is independent from hyperglycemic episodes.

The Average Daily Risk Range (ADRR) is a measure of glycemic variability based on both rl(BG) and rh(BG), which has been shown superior to traditional measures in terms of risk assessment and prediction of extreme glycemic excursions [16,17]. Specifically, it has been demonstrated that classification of risk for hypoglycemia based on four ADRR categories: Low Risk: ADRR <20; Low-Moderate Risk: 20≤ADRR<30; Moderate-High Risk: 30≤ADRR<40, and High Risk: ADRR>40, results in an over six-fold increase in risk for hypoglycemia from the lowest to the highest risk category [17].

SUMMARY OF THE INVENTION

An aspect of an embodiment of the present invention may comprise, but is not limited to, a method and system (and related computer program product) for tracking the probability for hypoglycemia from routine self-monitoring of blood glucose (SMBG) data in patients with diabetes. The method and system is based on, but is not limited to, a specific bivariate probability distribution of low BG events based jointly on the Low BG Index (LBGI) and the Average Daily Risk Range (ADRR).

The invention retrieves the data from a data source—typically a series of SMBG data of a patient available from the patient's meter—and allows tracking of the probability for future hypoglycemia over a predetermined duration, e.g. a 24 or 48 hour period. The tracking includes presentation of visual and/or numerical output, as well as construction of hypoglycemia risk trajectories that would enable warning messages for crossing of predefined thresholds, such as 50% likelihood for upcoming hypoglycemia below 50 mg/dl.

The related algorithm can have, but is not limited to, one of two modes of operation:

Mode 1—Sliding window: At every SMBG reading the algorithm evaluates the risk (probability) for hypoglycemia in the next predetermined period (e.g. 24 hours) and presents the results to the patient.

Mode 2—Daily cycle: Every evening, after all SMBG data for the day are collected (e.g. at the last SMBG reading for the day) the algorithm evaluates the risk (probability) for hypoglycemia in the next predetermined period (e.g. 24 hours) and presents the results to the patient;

It is contemplated that a meter implementation can have either of these two modes of use. A possible implementation combining Modes 1 and 2 would be for the algorithm to issue a warning for hypoglycemia in the next predetermined period (e.g. 24 hours) close to the last reading of the day, i.e. at a certain fixed time in the evening. If this is known in advance to the patient, the patient will be prompted to take a SMBG measure at bedtime, which is quite beneficial for getting a good daily profile. The time threshold (e.g. 9 PM) can be user-selected.

Experimental software has been developed (using MATLAB®) to illustrate one embodiment of the method. The software allows for computing the frequency of predictive messages at various BG or probability thresholds and in relationship to the frequency of SMBG recorded by the patient.

BRIEF DESCRIPTION OF THE DRAWINGS

FIGS. 3A and 3B are graphs showing percent prediction announcements (3A) and percent days without flags (3B) depending on ADRR and LBGI cutoff values;

FIGS. 4A and 4B are charts providing examples of the action of the method tracking the risk for hypoglycemia for two subjects.

DETAILED DESCRIPTION OF THE INVENTION

E.1. Theoretical Mathematical Base

Figure 1A:
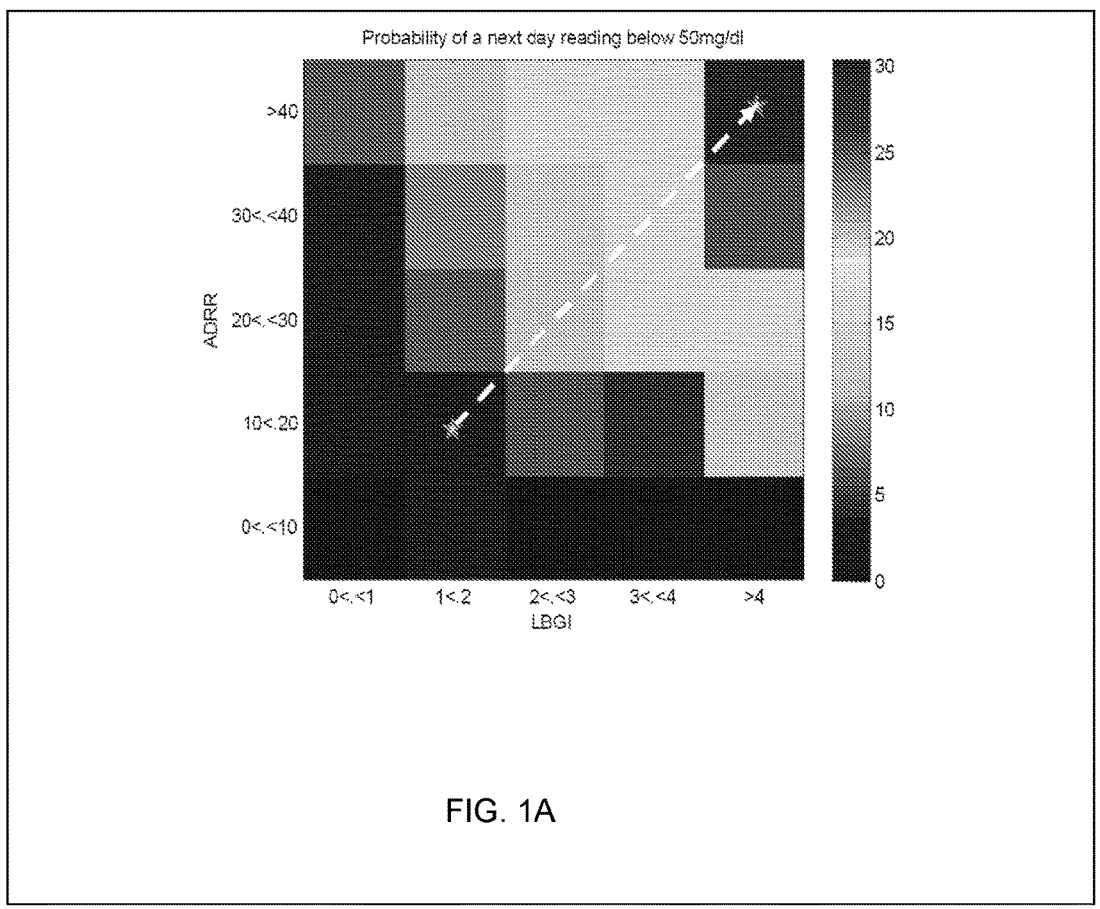
FIGS. 1A and 1B are graphs showing bivariate density of the probability for hypoglycemia below 50 mg/dl depending on the LBGI and ADRR.

One aspect of an embodiment of the present invention is a risk-tracking method and related system that, similarly to a weather forecast, projects the probability for hypoglycemia in the next 1-2 days using past ADRR and LBGI patterns. Some illustrative and non-limiting inventive steps are, for example:

1. Create a bivariate distribution mapping the probability for upcoming hypoglycemia to values of the ADRR and LBGI;
2. Optimize this distribution to achieve prediction of 51% of hypoglycemic episodes below 50 mg/dl 24 hours ahead, and
3. Track this distribution over time using routine SMBG readings of a patient with diabetes.

In order to do so, an embodiment of the invention predefines a sequence of time periods, which serve as basic time units for the analysis. With a frequency of 3-4 SMBG readings per day, a reasonable time period for assessing the ADRR is 14 days and a reasonable time period for assessing the LBGI is 48 hours. Thus, every day and with every SMBG reading we trace the ADRR from the last 14 days and the LBGI from the last 48 hours. This representation leads to a theoretical paradigm—the theory of random processes—which is frequently used to describe the evolution of individuals over time. In our case, an embodiment may use a random process with finite state space spanned over the values of the ADRR and LBGI and will describe the transitions of a subject across the levels of risk for hypoglycemia associated with this state space. This approach will provide the theoretical tools to estimate the likelihood for upcoming hypoglycemia within a predetermined period of time (e.g. the next 24 or 48 hours) and to investigate variants of the prediction dependent on BG level and frequency of SMBG.

The state space of this random process is the plane defined by the LBGI and ADRR, i.e. the continuous set of bivariate coordinates X={LBGI=x, ADRR=y}. At any time t the patient is within a certain subset $X_t$ of X defined as $X_t=\{x_1 \leq LBGI(t) < x_2, y_1 \leq ADRR(t) < y_2\}$, and each subset $X_t$ corresponds to a certain probability for hypoglycemia on the next day. Thus, the probability for hypoglycemia on the next day has the form:

$$P(t)=P(\text{hypoglycemia}|X_t), \text{ which is predetermined by the state of the patient } X_t \quad (3)$$

The specific formula of the mapping between $X_t$ and P(t) was established empirically as presented in the next section. The tracking of the risk of hypoglycemia for a patient will then be simply following the trajectory of the random process associated with this patient over time, and judging the probability for upcoming hypoglycemia by formula (3).

FIG. 1A illustrates this method by presenting a grayscale-coded rendition of the bivariate density of the probability for hypoglycemia below 50 mg/dl depending on the LBGI and ADRR, with higher probability for hypoglycemia on the next day coded in dark gray. For example, it is evident that if from one day to the next the person transits from a state {1≤LBGI<2, 10≤ADRR<20} to a state {4≤LBGI, 40≤ADRR}, his/her risk for hypoglycemia increases by 27% (3.5% to 30.5%, i.e. a 10-fold relative increase).

Figure 1B:
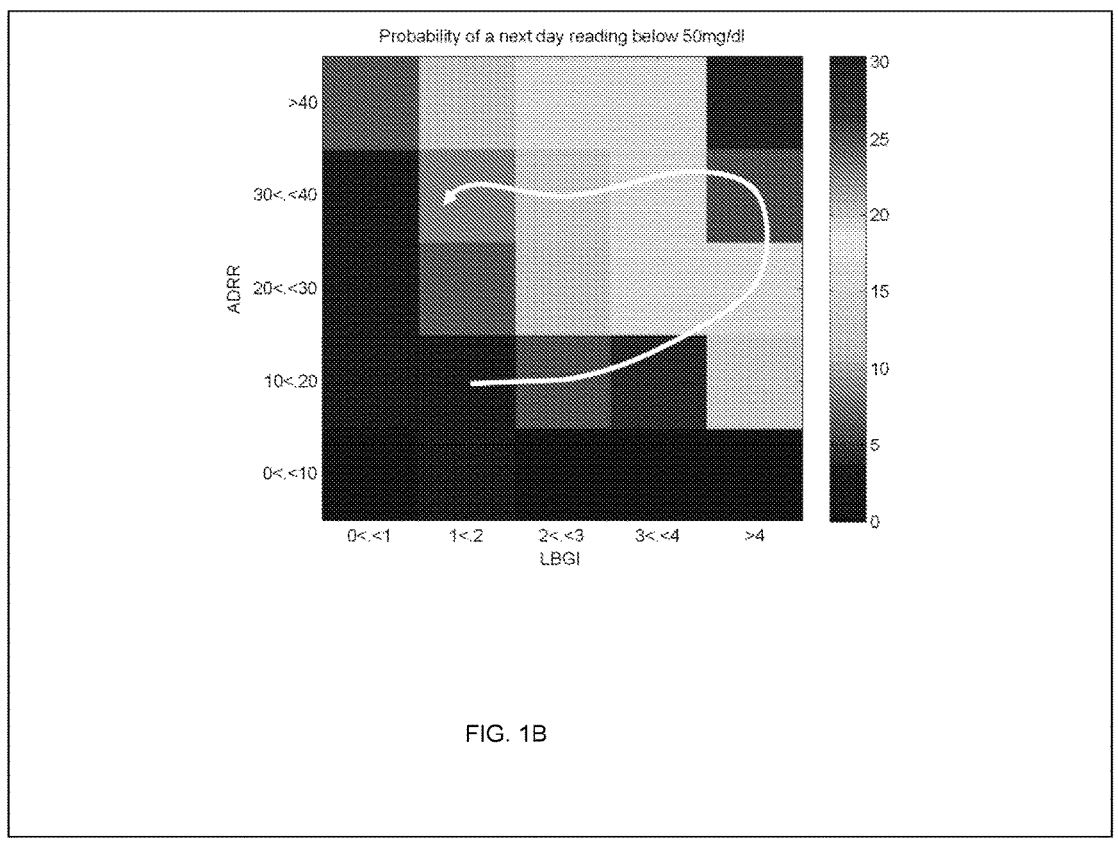

In general, the evolution of a person's risk for hypoglycemia over time is presented by a trajectory evolving within the LBGI/ADRR state space of FIG. 1A and at any point in time we would know the likelihood for hypoglycemia on the next day. A hypoglycemia-risk trajectory of an individual is illustrated in FIG. 1B.

E.2. Data Retrieval:

Let $x_1^1, x_2^1, \ldots x_n^1$ be a series of $n^1$ SMBG readings taken on Day 1;

Let $x_1^2, x_2^2, \ldots x_n^2$ be a series of $n^2$ SMBG readings taken on Day 2;

...

Let $x_1^M, x_2^M, \ldots x_n^M$ be a series of $n^M$ SMBG readings taken on Day $M$.

Where the number of days of observation is M=14 for this application (2 weeks).

Using formulas (1) and (2) introduced in the Background Section, we define:

$$LR^i = \max(rl(x_1^i), rl(x_2^i), \ldots, rl(x_n^i)) \text{ and}$$

$$HR^i = \max(rh(x_1^i), rh(x_2^i), \ldots, rh(x_n^i)) \text{ for day}\#i; i=1, 2, \ldots M.$$

The Average Daily Risk Range (ADRR) is then defined as:

$$ADRR = \frac{1}{M} \sum_{i=1}^{M} [LR^i + HR^i]$$

The Low BG Index (LBGI) is computed using the readings from the last two days of observation (day M−1 and day M) by the formula:

$$LBGI = \frac{1}{(n^{M-1} + n^M)} \left[ \sum_{s=1}^{n^{M-1}} rl(x_s^{M-1}) + \sum_{t=1}^{n^M} rl(x_t^M) \right]$$

This procedure is repeated at every SMBG reading for the LBGI and every day for the ADRR, yielding a sequence of paired values {LBGI(k), ADRR(k)} for each day of observation k=1, 2, 3, . . . , n. This sequence is the trajectory of the patient under observation over the state space of his/her Markov chain defined in the previous paragraph.

E.3. Mapping of {LBGI, ADRR} Pairs to Probability of Hypoglycemia in the Next 24 Hours:

To achieve this goal the method and system uses a "training" data set containing SMBG data for N=222 subjects with Type 1 diabetes. These subjects were monitored with SMBG for up to 4 months. The 222 subjects included in the training data were those who: (i) had at least 30 days of SMBG readings, and (ii) had at least 2 SMBG readings per day on average (e.g. someone with 60 readings over 30 days would be included, even if all readings are concentrated in one week). The demographic characteristics of these subjects are presented in Table 1.

TABLE 1

Training Data (N = 222 subjects with T1DM) used to establish the relationship between {LBGI, ADRR} pairs and probability for hypoglycemia

| Age (years) | 32.3 (SD = 17.6) | SMBG frequency (readings/day) | 4.4 (SD = 1.9) |
|---|---|---|---|
| Gender (% male) | 46.0% | Average BG | 190.3 (SD = 40.4) |
| BMI | 24.0 (SD = 4.8) | Baseline LBGI | 2.42 (SD = 2.1) |
| Baseline HbA1c | 8.1 (SD = 1.2) | Readings <= 70 mg/dl | 10.8% |
| Years of diabetes | 15.4 (SD = 12.2) | Readings <= 50 mg/dl | 3.7% |
| Duration of study (days) | 80.5 (SD = 28.3) | Baseline ADRR | 42.1 (SD = 13.9) |

The training data set was used to map the values of the pairs {LBGI, ADRR} to the probability for significant hypoglycemia, defined as BG reading ≤50 mg/dl, in the subsequent 24 hours. Other variables were considered for inclusion in the algorithm, but were rejected upon examination. The final algorithm used the SMBG data to compute:

The LBGI computed from the SMBG readings in the preceding 48 hours, and

The ADRR computed from the SMBG readings in the preceding 14 days.

Figure 2A:
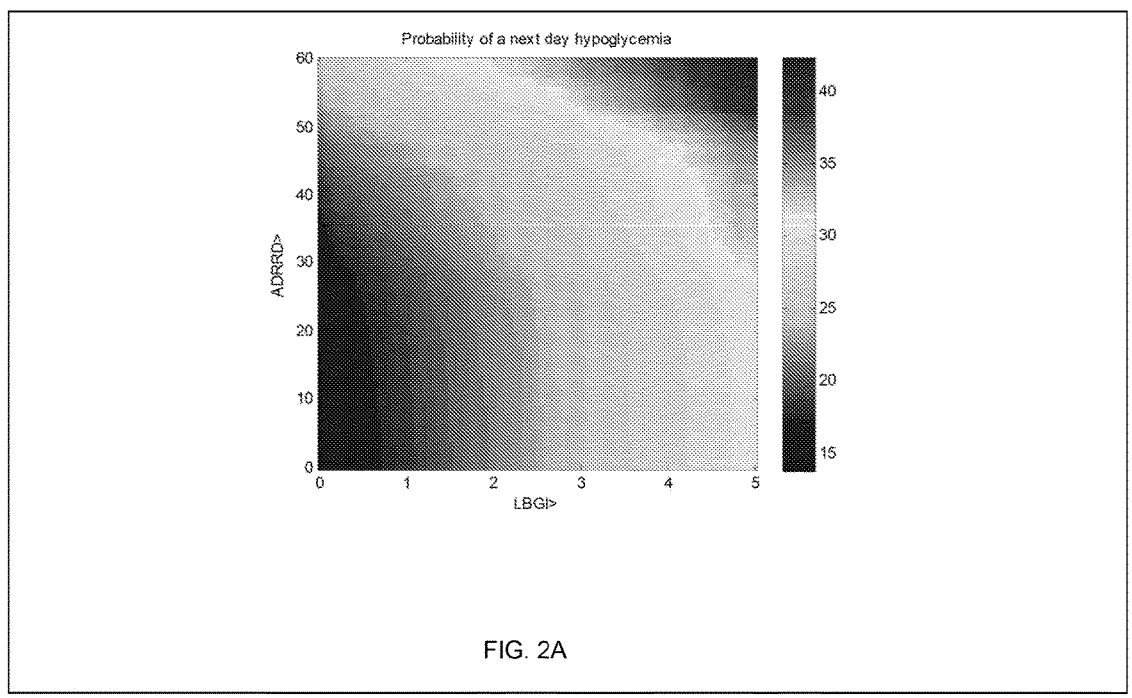
FIGS. 2A and 2B are graphs showing empirical (2A) and theoretical (2B) likelihood for a hypoglycemic episodes below 50 mg/dl within 24 hours when ADRR and LBGI exceed certain cutoff values.

The probabilities for hypoglycemia 50 mg/dl increased uniformly with the increase of both the LBGI and the ADRR cutoff values (FIG. 2A). This graphical representation provided the empirical probabilities used to estimate the mapping formula (1).

The estimation resulted in the following formula that represents the conditional probability for hypoglycemia below 50 mg/dl, given LBGI and ADRR are greater than known thresholds:

$$P(Hypo \mid ADRR > x \,\&\, LBGI > y) = a(y) + (100 - a(y)) \frac{\left(\frac{x}{b(y)}\right)^{c(y)}}{1 + \left(\frac{x}{b(y)}\right)^{c(y)}} \quad (4)$$

$$a(y) = \alpha_a + \beta_a y$$

$$b(y) = \alpha_b + \beta_b y$$

$$c(y) = \alpha_c + \beta_c \frac{\left(\frac{y}{\delta_c}\right)^{\gamma_c}}{1 + \left(\frac{y}{\delta_c}\right)^{\gamma_c}}$$

In other words, formula (4) is the equivalent of the theoretical formula (3), which is derived from the training data. In this case all subsets of the state space X have the common appearance: $X_t(x,y) = \{ADRR > x \,\&\, LBGI > y\}$. The values of the parameters in formula (4) have been determined to be:

$\alpha_a = 15.1$ range: [5,20]

$\beta_a = 3.13$ range: [1,5]

$\alpha_b = 116$ range: [50,150]

$\beta_b = -5.66$ range: [−10,0]

$\alpha_c = 2.9$ range: [1,5]

$\beta_c = 1$ range: [1,5]

$\delta_c = 2.35$ range: [1,10]

$\gamma_c = 3.76$ range: [1,5]

Figure 2B:
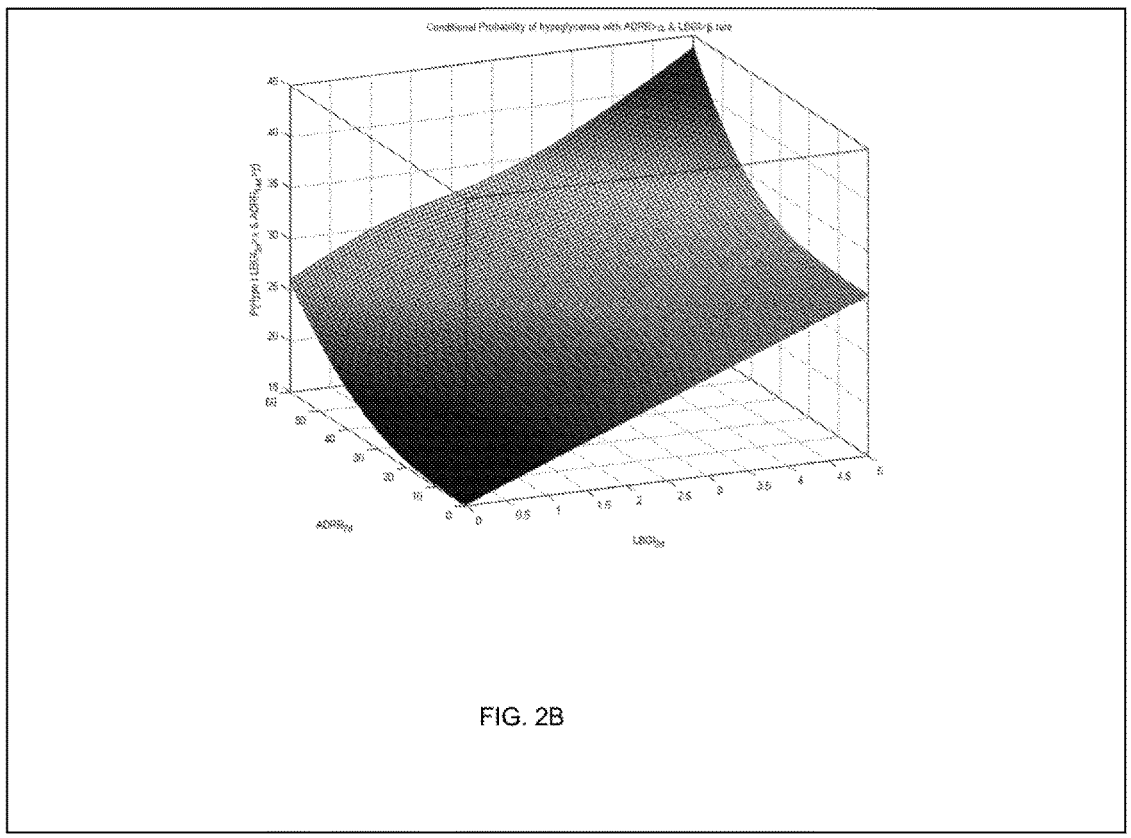

FIG. 2B presents the 3-dimensional graph of the probability defined by formula (2) with these specific parameter values.

It is important to note that the values of each parameter can fluctuate within certain ranges as presented above, and that different implementations of the method could use different sets of parameter values.

E.4. Construction of a Hypoglycemia Detection (Flag-Raising) Rule:

Table 2 presents the conditional probability for upcoming hypoglycemia when LBGI and ADRR exceed certain thresholds, i.e., the probability for a reading <50 mg/dl in the 24 hours following LBGI and ADRR exceeding of these thresholds (i.e. the same function that is presented graphically in FIG. 2A).

TABLE 2

Mapping Between {LBGI > x, ADRR > y} pairs and probability for hypoglycemia

| ADRR | LBGI | | | | | | | | | | |
|---|---|---|---|---|---|---|---|---|---|---|---|
| | 0.0 | 0.5 | 1.0 | 1.5 | 2.0 | 2.5 | 3.0 | 3.5 | 4.0 | 4.5 | 5.0 |
| 0 | 13.8 | 16.5 | 18.3 | 20.0 | 21.7 | 23.3 | 24.5 | 26.1 | 27.6 | 29.1 | 30.6 |
| 5 | 13.9 | 16.5 | 18.4 | 20.1 | 21.7 | 23.3 | 24.5 | 26.1 | 27.6 | 29.1 | 30.6 |
| 10 | 14.0 | 16.7 | 18.5 | 20.2 | 21.8 | 23.4 | 24.5 | 26.1 | 27.6 | 29.1 | 30.6 |
| 15 | 14.2 | 16.9 | 18.7 | 20.3 | 21.9 | 23.5 | 24.6 | 26.3 | 27.7 | 29.2 | 30.7 |
| 20 | 14.5 | 17.1 | 18.8 | 20.5 | 22.0 | 23.6 | 24.7 | 26.3 | 27.8 | 29.3 | 30.7 |
| 25 | 14.8 | 17.4 | 19.1 | 20.7 | 22.2 | 23.8 | 24.9 | 26.5 | 28.1 | 29.6 | 31.0 |
| 30 | 15.6 | 18.2 | 19.9 | 21.6 | 23.1 | 24.6 | 25.8 | 27.3 | 29.0 | 30.5 | 31.9 |
| 35 | 16.6 | 19.4 | 21.0 | 22.5 | 23.9 | 25.4 | 26.5 | 28.0 | 29.7 | 31.5 | 32.8 |
| 40 | 17.7 | 20.3 | 21.8 | 23.3 | 24.6 | 26.1 | 27.1 | 28.7 | 30.5 | 32.1 | 33.5 |
| 45 | 19.4 | 21.8 | 23.2 | 24.7 | 25.7 | 27.0 | 28.1 | 29.7 | 31.5 | 33.2 | 34.8 |
| 50 | 21.2 | 23.7 | 25.0 | 26.6 | 27.5 | 28.6 | 29.7 | 31.3 | 33.2 | 34.9 | 37.1 |
| 55 | 23.2 | 25.7 | 27.2 | 28.8 | 29.8 | 30.9 | 32.5 | 34.4 | 36.5 | 39.6 | 41.1 |
| 60 | 24.7 | 27.5 | 29.2 | 31 | 32.2 | 33.4 | 35 | 36.7 | 38.4 | 40.2 | 42.3 |

After the mapping between the {LBGI, ADRR} thresholds and the probability for subsequent significant hypoglycemia has been established, it is evident that higher ADRR and LBGI over the studied period (14 and 2 days) are highly predictive of an upcoming hypoglycemic episode and therefore a hypoglycemia detection rule can be derived as follows: when specific conditions on ADRR and LBGI are met a "flag" is raised: i.e. a future hypoglycemia event is predicted. As the probability of hypoglycemia has been shown to be increasing with LBGI and ADRR, a rule of the form shown below is particularly relevant:

$$\text{flag} = \begin{cases} 1 & \text{if } ADRR > x \text{ \& } LBGI > y \\ 0 & \text{otherwise} \end{cases}$$

From Table 2, optimal cutoffs were determined that predicted 50% of all significant hypoglycemic episodes with a minimum number of inaccurate "flags," i.e. minimum number of occasions when hypoglycemia was predicted, but an episode was not encountered. FIG. 3A presents the percent hypoglycemic episodes that were predicted, while FIG. 3B presents the percent of days without flags. The optimal value is the dark gray zone of the two figures, which corresponds to cutoffs of LBGI≥3.5 and ADRR≥30.

E.5. Tracking of the Probability for Imminent Hypoglycemia:

FIGS. 4A and 4B are charts presenting examples of the tracking of the probability for hypoglycemia depending on the trajectory of the process X(t) for each of two presented subjects. At any point in time the subject state X(t) is determined from the LBGI value computed over the last 48 hours and the ADRR value computed from the last 14 days. Then, formula (3) is used to assign a probability for upcoming hypoglycemia. When this probability is high (i.e. exceeds a preset threshold), a "flag" is raised warning for an upcoming hypoglycemia event. It is evident that in FIG. 4A the "flag" is raised quite frequently. Because this patient experienced frequent hypoglycemia, FIG. 4A confirms the ability of the method to predict such episodes. Conversely, in FIG. 4B the flag is raised only once. This coincides with the fact that this patient did not experience significant hypoglycemic episodes during the observation.

E.6. Data Restrictions:

We re-emphasize that, in a non-limiting approach, the only requirement for a subject to be included in the test data set was to have a certain number of SMBG readings amounting to an average of ≥2 readings/day during the study. This is similar to minimum-data criteria that were previously used in other algorithms. Because this criterion does not imply that we would have 2 or more readings every day, various testing frequency situations are investigated below. In addition:

No restrictions were imposed on the number of readings used to compute the LBGI—even one reading in a day would generate prediction for the next day;

ADRR was computed only on days that have 3 or more SMBG readings, but the number of days with 3 or more readings during the preceding 14 days is not restricted. For example, if only one out of 14 days includes >3 SMBG readings, the ADRR is computed and the results are included in the tables below.

F. Validation of the Method and Investigation of the Influence of Testing Frequency, Prediction Horizon, and Blood Glucose Threshold F.1. Test Data Set:

To validate the method we used an independent test data set, which included SMBG data for N=179 subjects with Type 1 (N=91) and Type 2 diabetes (N=88) who were monitored with SMBG readings for 4-6 months. Similarly to the training data, these subjects met the two conditions: (i) at least 30 days of SMBG readings, and (ii) at least 2 SMBG readings per day on average. Their characteristics are presented in Table 3.

In addition to demographic and biometric characteristics, Table 3 includes a number of study parameters, including the average duration of study, the SMBG frequency during the study, as well as key SMBG parameters, such as average BG, percent readings below 70 mg/dl and 50 mg/dl, LBGI, and ADRR.

TABLE 3

Test Data

|  | T1DM (N = 91 subjects) | T2DM (N = 88 subjects) |
|---|---|---|
| Age (years) | 40.4 (SD = 11.2) | 50.6 (SD = 8.2) |
| Gender (% male) | 44.9% | 42.1% |
| BMI | 25.6 (SD = 4.5) | 35.4 (SD = 8.9) |
| Baseline HbA1c | 7.6 (SD = 1.25) | 8.5 (SD = 2.0) |
| Years of diabetes | 19.7 (SD = 10.9) | 11.4 (SD = 8.4) |
| Duration of study (days) | 200.5 (57.0) | 116.3 (27.3) |
| SMBG readings/day | 5.0 (SD = 2.0) | 3.4 (SD = 0.66) |
| Average BG | 170.7 (SD = 36.9) | 178.5 (SD = 49.9) |
| Baseline LBGI | 2.91 (SD = 2.35) | 0.75 (SD = 1.1) |
| Readings <= 70 mg/dl | 12.9% | 4.0% |
| Readings <= 50 mg/dl | 4.4% | 2.1% |
| Baseline ADRR | 37.8 (SD = 11.6) | 22.8 (SD = 13.5) |

As seen from Tables 1 and 3, the T1DM subjects in the test data are similar to the subjects in the training data set, while the individuals with T2DM are different in terms of demographic and biometric characteristics, glucose variability, and frequency of hypoglycemia. This variation adds external validity to the prediction method.

F.2. Overall Results:

The total number of days of observation in this data set was 30,757 of which 28,480 had at least one SMBG reading. These 28,480 days included 18,247 days of observation in T1DM and 10,233 days of observation in T2DM. The number of days with hypoglycemic episodes 50 mg/dl recorded during the study was 3,148 (2,974 in T1DM and 174 in T2DM), which amounts to overall baseline frequency of days with hypoglycemia 50 mg/dl of 10.2% (or 11.1% if only days with SMBG are used; 16.3% in T1DM and 1.7% in T2DM). Table 4 presents the results obtained in this data set without any restrictions on testing frequency.

TABLE 4

PREDICTION OF HYPOGLYCEMIA

| | |
|---|---|
| Percent of all hypoglycemic episodes <=50 mg/dl predicted by the algorithm within 24 hours from "raising a hypoglycemia flag" | 52.8% |
| Percent inaccurate flags (hypoglycemia predicted, but no episode occurring) | 10.6% |
| Percent of total flagged days | 15.9% |
| Likelihood of hypoglycemia <=50 mg/dl on the day after the flag is raised | 33.3% |

The bold numbers in Table 4 reflect the optimization criteria used in the analysis of training data. It is evident that in the test data set the percent predicted hypoglycemic episodes holds above 50%, and is even slightly better than the training data. This is accompanied by 10.6% of days when a flag would be raised inappropriately and by 15.9% of total days with flag raised. In other words, a flag would be raised once a week on average, and inappropriate flag would be raised once in 10 days. The likelihood for hypoglycemia 50 mg/dl is 33.3% after a flag is raised, which is 3-fold higher than the baseline frequency.

F.3. Testing Frequency Analysis:

Table 5 presents the dependence of the accuracy of prediction on the frequency of testing. This is done by raising the flag only on days that have a minimum of 2, 3, 4, 5, or 6 SMBG readings. The assumption is that if there is appropriate number of readings, there is a flag (or indication of no flag) for the next day. If there are an insufficient number of readings, no prediction can be made either way and the algorithm remains silent (or says not enough readings). Thus, the hypoglycemic episodes that might occur after a day with insufficient readings are not counted as a prediction or false alarm. The rows in Table 5 are the same as in Table 4; the last line presents the number and percent of days that satisfy the number-of-readings requirement (e.g. if the restriction is imposed, the algorithm will remain silent in (100-this percentage) of days.

TABLE 5

Minimum Number Of Readings to Calculate a Flag for the Next Day

| | ≥2 | ≥3 | ≥4 | ≥5 | ≥6 |
|---|---|---|---|---|---|
| % hypoglycemia predicted | 53.2 | 54.0 | 57.1 | 63.2 | 71.5 |
| % inaccurate flags | 10.3 | 9.6 | 8.5 | 6.3 | 3.0 |
| % total flagged days | 15.6 | 14.7 | 13.0 | 9.9 | 5.3 |
| Likelihood for hypoglycemia on the next day | 33.7 | 34.4 | 34.9 | 36.6 | 42.7 |
| Percent days meeting the condition | 27,181 (95.4%) | 24,335 (85.4%) | 19,080 (67.0%) | 9,595 (33.7%) | 4,052 (14.2%) |

It is evident that, while testing frequency improves the prediction, most improvement occurs at quite high (and therefore unrealistic) testing frequencies. We can say, however, that "if you test 3 times every day, you'll get 54% of all days with episodes ≤50 flagged 24 hours in advance, with less than 10% of days including inaccurate flags.

F.4. Flagging Rate Analysis:

Table 6 presents the percent of subjects in several flagging rate categories, beginning with 0 flags throughout the study to above 50% of days flagged. The method and system also includes the average % of days with hypoglycemia <=50 mg/dl for each flagging category. It is evident that higher flagging rate is related to higher frequency of hypoglycemic episodes:

TABLE 6

Percent Days Flagged

| | | 0 | 0<-5% | 5-10% | 10-30% | 30-50% | ≥50% |
|---|---|---|---|---|---|---|---|
| All Subjects | Number of subjects | 84 | 23 | 14 | 25 | 17 | 16 |
| | % subjects | 46.9% | 12.8% | 7.8% | 14.0% | 9.5% | 8.9% |
| | % days with hypo | 0.6% | 2.2% | 4.6% | 10.8% | 23.2% | 42.9% |
| T1DM | Number of subjects | 9 | 15 | 13 | 22 | 17 | 15 |
| | % subjects | 9.9% | 16.5% | 14.3% | 24.2% | 18.7% | 16.5% |
| | % days with hypo | 0.6% | 2.4% | 4.8% | 10.4% | 23.2% | 43.7% |

TABLE 6-continued

|  |  | Percent Days Flagged | | | | | |
|---|---|---|---|---|---|---|---|
|  |  | 0 | 0<-5% | 5-10% | 10-30% | 30-50% | ≥50% |
| T2DM | Number of subjects | 75 | 8 | 1 | 3 | 0 | 1 |
|  | % subjects | 85.2% | 9.1% | 1.1% | 3.4% | 0.0% | 1.1% |
|  | % days with hypo | 0.6% | 1.5% | 2.1% | 15.3% | 0 | 24.6% |

From Table 6 we can conclude that people who get frequent flags have indeed high rate of hypoglycemia, comparable to flag frequency. Thus, if the flag works as intended and prompts appropriate corrective actions, the frequency of hypoglycemia should go down, and the frequency of flagging should go down as well.

F.5. Personalized Flagging Thresholds:

In addition, we could consider setting different thresholds for subjects at different frequencies of hypoglycemia, e.g. we could use the LBGI or the frequency of SMBG readings below a certain threshold to adjust automatically the flag raising thresholds every two weeks. Alternatively (and this is probably the better option) a threshold could be preset by the subject, i.e. a patient could decide to limit the frequency of flagging to a certain percentage of days, which would automatically shift the ADRR/LBGI thresholds for flagging to higher values.

Table 7a presents such a scenario for all subjects in the test data set, gradually increasing the thresholds for ADRR and LBGI from their current values of 30 and 3.5 (in Table 4). Such an increase could be automatic, depending on observed frequency of flagging, or user-initiated by patient choice.

Table 7b presents gradual increase of the ADRR and LBGI threshold in subjects who were in the top 25% flagging rate with the preset thresholds of 30 and 3.5. It is evident that for these subjects the flagging rate can be significantly decreased with threshold increase. Because baseline prediction of hypoglycemia in these subjects is better, a certain decrease in flagging rate can be done without compromising the prediction probability to below 50%.

TABLE 7a

| | Gradually Increasing ADRR and LBGI Thresholds | | | | |
|---|---|---|---|---|---|
| Whole population | ADRR ≥ 30 LBGI ≥ 3.5 | ADRR ≥ 35 LBGI ≥ 3.5 | ADRR ≥ 40 LBGI ≥ 4.0 | ADRR ≥ 45 LBGI ≥ 4.5 | ADRR ≥ 50 LBGI ≥ 5.0 |
| % hypoglycemia predicted | 52.8% | 43.5% | 29.9% | 21.8% | 16.2% |
| % inaccurate flags | 10.6% | 8.1% | 4.8% | 2.8% | 1.7% |
| % total flagged days | 15.9% | 12.5% | 7.8% | 5% | 3.3% |
| Likelihood for hypoglycemia on the next day | 33.3% | 35.0% | 38.6% | 43.8% | 49.0% |

TABLE 7b

| | Gradually Increasing ADRR and LBGI Thresholds | | | | |
|---|---|---|---|---|---|
| Ss at top 25% flag frequency | ADRR ≥ 30 LBGI ≥ 3.5 | ADRR ≥ 35 LBGI ≥ 3.5 | ADRR ≥ 40 LBGI ≥ 4.0 | ADRR ≥ 45 LBGI ≥ 4.5 | ADRR ≥ 50 LBGI ≥ 5.0 |
| % hypoglycemia predicted | 62.0% | 51.9% | 36.1% | 26.3% | 19.6% |
| % inaccurate flags | 27.9% | 22.8% | 14.2% | 8.4% | 5.2% |
| % total flagged days | 44.6% | 36.7% | 23.9% | 15.5% | 10.5% |
| Likelihood for hypoglycemia on the next day | 37.3% | 38.0% | 40.6% | 45.5% | 50.2% |

F.6. Correlation between Testing Frequency and Flagging Rate

For each subject in the test data set we compute the following variables:

Frequency of raised flags per day of study;
Average number of SMBG readings per day;
Percent of readings <=70 mg/dl and percent readings <=50 mg/dl. The correlation between testing and flag frequency was positive: R=0.45, p<0.01.

However, this correlation was entirely accounted for by the frequency of low BG episodes. More precisely, the correlation of testing frequency with the percentage of BG readings below 70 mg/dl was similar R=0.4, p<0.01.

To assess the relative importance of testing frequency and occurrence of hypoglycemia for flagging, we perform a linear regression with flag frequency as the dependent variable and testing frequency, BGs≤70 mg/dl and BGs≤50 mg/dl as predictors. The regression shows that the percentages of low BG readings are the primary predictors of flag frequency, explaining over 80% of the variance of flagging frequency (R-square=81%). When added to the equation, testing frequency increases R-square to 82%, i.e. explains less than 1% of the frequency of flagging and is not significant.

Thus, an important conclusion can be made: While, superficially, flagging frequency is correlated with the frequency of testing, more frequent testing is entirely driven by more frequent hypoglycemia. Naturally, by algorithm design, more frequent hypoglycemia would result in more frequent flagging. Therefore flagging frequency is not directly related to frequency of testing. Any apparent relationship is mediated and entirely determined by the frequency of hypoglycemic episodes.

F.7. Analysis of 48-Hour Prediction Horizon:

We now go back to the previously preset ADRR/LBGI thresholds of 30 and 3.5 and investigate the influence on the prediction horizon. Specifically, we increase the prediction horizon from 24 to 48 hours ahead. Table 8 presents results analogous to Table 2 in the case of 48-hour prediction. It is clear that, while the percentage of flag raising remains the same, all other numbers are favorably influenced. In particular, the prediction rate increases by 10% and the likelihood for subsequent hypoglycemia within the subsequent 48 hours is significantly improved:

TABLE 8

PREDICTION OF HYPOGLYCEMIA

| | |
|---|---|
| Percent of all hypoglycemic episodes <=50 mg/dl predicted by the algorithm within 48 hours from "raising a hypoglycemia flag" | 62.3% |
| Percent inaccurate flags (hypoglycemia predicted, but no episode occurring) | 8.6% |
| Percent of total flagged days | 15.9% |
| Likelihood of hypoglycemia <=50 mg/dl on the day after the flag is raised | 49.9% |

F.8. Analysis of BG Prediction Target of 70 mg/dl:

Finally, we redefine the prediction target from 50 mg/d to 70 mg/dl to see what would be the rate of prediction of mild hypoglycemia. Doing so we have two options for flagging:

First, we can use the exact settings of the flag that were used for prediction of 50 mg/dl above. Table 9a presents these results for both 24- and 48-hour prediction horizons. The overall number of days with hypoglycemic episodes <=70 mg/dl recorded during the study was 7,569 (7,569 in T1DM and 891 in T2DM), which amounts to overall baseline frequency of days with hypoglycemia ≤70 mg/dl of 29.7% (41.5% in T1DM and 8.7% in T2DM). Thus, following a flag the likelihood of occurrence of hypoglycemia ≤70 mg/dl essentially doubles.

TABLE 9a

PREDICTION OF HYPOGLYCEMIA

| | 24 h horizon | 48 h horizon |
|---|---|---|
| Percent of all hypoglycemic episodes <=70 mg/dl predicted by the algorithm. | 35.8% | 44.7% |
| Percent inaccurate flags (hypoglycemia predicted, but no episode occurring) | 6.6% | 3.6% |
| Percent of total flagged days | 15.9% | 15.9% |
| Likelihood of hypoglycemia <=70 mg/dl on the day after the flag is raised | 61.8% | 78.8% |

Second, using training data we optimize the ADRR and LBGI threshold to specifically predict BG<=70 mg/dl, which leads to the thresholds ADRR>20 and LBGI>2.5. As seen in Table 9b, with this specific optimization the % predicted hypoglycemia rises above 50%, with quite low rate of inaccurate flagging and likelihood for subsequent hypoglycemia approaching 60% within 24 hours and 75% within 48 hours.

TABLE 9b

PREDICTION OF HYPOGLYCEMIA

| | 24 h horizon | 48 h horizon |
|---|---|---|
| Percent of all hypoglycemic episodes <=70 mg/dl predicted by the algorithm. | 52% | 62.0% |
| Percent inaccurate flags (hypoglycemia predicted, but no episode occurring) | 11.7% | 6.8% |
| Percent of total flagged days | 27.1% | 27.1% |
| Likelihood of hypoglycemia ≤70 mg/dl on the day after the flag is raised | 57% | 75.1% |

In summary, an aspect of the present invention provides a method and system (and related computer program product) for, but not limited thereto, tracking the probability of hypoglycemia from SMBG, which has been developed on a large training data set containing SMBG data for 222 individuals with T1DM and was then tested in an independent test data set of N=179 individuals: N=91 with T1DM and N=88 with T2DM (Tables 1 and 3).

Out of many considered variables, the LBGI (computed over 48 hours) and the ADRR (computed over 14 days) appear to be the best combination for predicting of hypoglycemic episodes. The probabilities for subsequent significant hypoglycemia, given a pair of values {LBGI, ADRR} are given in Table and in FIGS. 2A and 2B. This allows tracking the probability for significant hypoglycemia over time as presented in FIG. 1B.

Thorough investigation of the algorithm yielded the following results:

The optimal cutoff is LBGI≥3.5 and ADRR≥30, which achieved prediction of over 50% of hypoglycemic episodes below 50 mg/dl in the subsequent 24 hours (Table 4), i.e. with this cutoff over half of hypoglycemic episodes below 50 mg/dl are "flagged" up to 24 hours in advance;

The precision of hypoglycemia prediction increases with testing frequency (Table 5);

Most subjects with T2DM and some subjects with T1DM who rarely experience hypoglycemia would never get a flag (Table 6);

In general, the flagging frequency is almost entirely predetermined by the frequency of hypoglycemic episodes, and is not dependent on the frequency of testing;

For patients with very high rates of hypoglycemia the flagging frequency can be reduced automatically, or by the user (Tables 7A and 7B);

The prediction horizon can be increased from 24 to 48 hours, which would improve the results substantially (Table 8);

Hypoglycemic episodes ≤70 mg/dl are reasonably well predicted by the algorithm without changing its parameters (Table 9A), or the prediction can be optimized for this specific BG target (Table 9B).

An aspect of an embodiment of the present invention provides a method and system (and related computer program product) for, but not limited thereto, tracking that includes presentation of visual and numerical output, as well as construction of hypoglycemia risk profile that would enable messages warning of future crossings of predefined thresholds. Thus, the system and method may have, but not limited thereto, the following SMBG-related applications:

Track the risk for upcoming hypoglycemia from routine SMBG data;

Alert the user (patient or health-care provider) about elevated chances for upcoming hypoglycemia;

Provide customization of the alerts for upcoming hypoglycemic events in terms of their magnitude (e.g. below 50 mg/dl or below 70 mg/dl) or time frame of forecast (e.g. next 24 or next 48 hours);

The hypoglycemia risk-tracking information is intended for physicians, health-care professionals, and patients with diabetes. In test data, over 50% of the upcoming within 24 hours hypoglycemic episodes ≤50 mg/dl have been predicted.

Blood glucose self-monitoring devices allow observational practice in diabetes, providing routine SMBG data that serves as the main feedback enabling patients to maintain their glycemic control. An aspect of an embodiment of the present invention may be utilized for a number of products and services, such as but not limited thereto, the following SMBG-related applications:

Track the risk for upcoming hypoglycemia from routine SMBG data;

Alert the user (patient or health-care provider) about elevated chances for upcoming hypoglycemia;

Provide customization of the alerts for upcoming hypoglycemic events in terms of their magnitude (e.g. below 50 mg/dl or below 70 mg/dl) or time frame of forecast (e.g. next 24 or next 48 hours);

The hypoglycemia risk-tracking information is intended for physicians, health-care professionals, and patients with diabetes.

An advantage of the method and system is, but not limited thereto, in test data, over 50% of the upcoming within 24 hours hypoglycemic episodes ≤50 mg/dl have been predicted, which has not been achieved by any other method.

Figure 5:
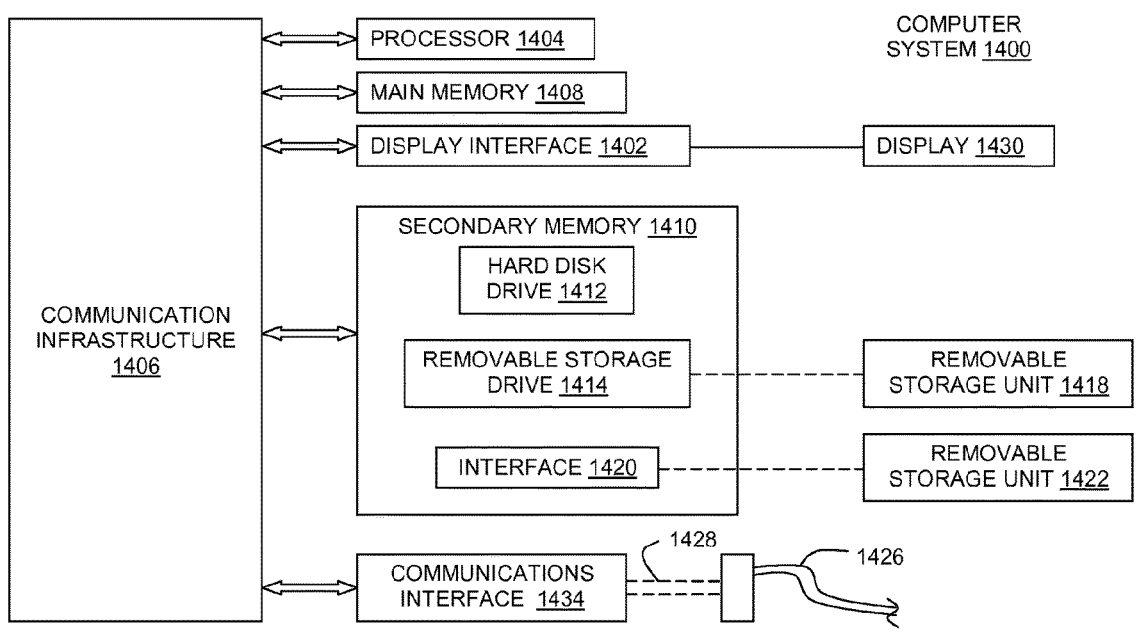
FIG. 5 is a functional block diagram of a computer system for implementation of an exemplary embodiment or portion of an embodiment of the present invention.

FIG. 5 is a functional block diagram for a computer system 1400 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digital assistants (PDAs) equipped with adequate memory and processing capabilities. In an example embodiment, the invention was implemented in software running on a general purpose computer as illustrated in FIG. 14. The computer system 1400 may includes one or more processors, such as processor 1404. The Processor 1404 is connected to a communication infrastructure 1406 (e.g., a communications bus, cross-over bar, or network). The computer system 1400 may include a display interface 1402 that forwards graphics, text, and/or other data from the communication infrastructure 1406 (or from a frame buffer not shown) for display on the display unit 1430. Display unit 1430 may be digital and/or analog.

The computer system 1400 may also include a main memory 1408, preferably random access memory (RAM), and may also include a secondary memory 1410. The secondary memory 1410 may include, for example, a hard disk drive 1412 and/or a removable storage drive 1414, representing a floppy disk drive, a magnetic tape drive, an optical disk drive, a flash memory, etc. The removable storage drive 1414 reads from and/or writes to a removable storage unit 1418 in a well known manner. Removable storage unit 1418, represents a floppy disk, magnetic tape, optical disk, etc. which is read by and written to by removable storage drive 1414. As will be appreciated, the removable storage unit 1418 includes a computer usable storage medium having stored therein computer software and/or data.

In alternative embodiments, secondary memory 1410 may include other means for allowing computer programs or other instructions to be loaded into computer system 1400. Such means may include, for example, a removable storage unit 1422 and an interface 1420. Examples of such removable storage units/interfaces include a program cartridge and cartridge interface (such as that found in video game devices), a removable memory chip (such as a ROM, PROM, EPROM or EEPROM) and associated socket, and other removable storage units 1422 and interfaces 1420 which allow software and data to be transferred from the removable storage unit 1422 to computer system 1400.

The computer system 1400 may also include a communications interface 1424. Communications interface 1424 allows software and data to be transferred between computer system 1400 and external devices. Examples of communications interface 1424 may include a modem, a network interface (such as an Ethernet card), a communications port (e.g., serial or parallel, etc.), a PCMCIA slot and card, a modem, etc. Software and data transferred via communications interface 1424 are in the form of signals 1428 which may be electronic, electromagnetic, optical or other signals capable of being received by communications interface 1424. Signals 1428 are provided to communications interface 1424 via a communications path (i.e., channel) 1426. Channel 1426 (or any other communication means or channel disclosed herein) carries signals 1428 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 1414, a hard disk installed in hard disk drive 1412, and signals 1428. These computer program products ("computer program medium" and "computer usable medium") are means for providing software to computer system 1400. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 1408 and/or secondary memory 1410. Computer programs may also be received via communications interface 1424. Such computer programs, when executed, enable computer system 1400 to perform the features of the present invention as discussed herein. In particular, the computer programs, when executed, enable processor 1404 to perform the functions of the present invention. Accordingly, such computer programs represent controllers of computer system 1400.

In an embodiment where the invention is implemented using software, the software may be stored in a computer program product and loaded into computer system 1400 using removable storage drive 1414, hard drive 1412 or communications interface 1424. The control logic (software or computer program logic), when executed by the processor 1404, causes the processor 1404 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

PUBLICATIONS

The following patents, applications and publications as listed below and throughout this document are hereby incorporated by reference in their entirety herein.

The devices, systems, methods and computer program products of various embodiments of the invention disclosed herein may utilize aspects disclosed in the following references, applications, publications and patents and which are hereby incorporated by reference herein in their entirety:

1. Aaby Svendsen P, Lauritzen T, Soegard U, Nerup J. Glycosylated Haemoglobin and Steady-State Mean Blood Glucose Concentration in Type 1 (Insulin-Dependent) Diabetes. *Diabetologia*, 23: 403-405, 1982.

2. Brownlee M, Hirsh I B. Glycemic Variability: A hemoglobin Alc—Independent Risk Factor for Diabetic Complication? *JAMA* 2006 295: 1707-1708.

3. Cryer P E. Hypoglycaemia: The limiting factor in the glycaemic management of type I and type II diabetes. *Diabetologia* 45: 937-948, 2002

4. Cryer P E. Iatrogenic hypoglycemia as a cause of hypoglycemia-associated autonomic failure in IDDM: A vicious cycle. *Diabetes* 41:255-260, 1992

5. Cox D J, Gonder-Frederick L A, Ritterband L, Clarke W L, and Kovatchev B P (2007). Prediction of Severe Hypoglycemia. *Diabetes Care*, 30: 1370-1373.

6. Gold A E, Deary I J, Frier B M. Recurrent severe hypoglycaemia and cognitive function in type I diabetes. *Diabet Med* 10:503-508, 1993

7. Henderson J N, Allen K V, Deary I J, Frier B M. Hypoglycemia in insulin-treated Type 2 diabetes: frequency, symptoms and impaired awareness. *Diabet Med* 20: 1016-1021, 2003

8. Klonoff D C: Continuous glucose monitoring: roadmap for $21^{st}$ century diabetes therapy. Diabetes Care 2005; 28:1231-1239.

9. Kovatchev B P, Cox D J, Farhy L S, Straume M, Gonder-Frederick L A, Clarke, W L. (2000) Episodes of Severe Hypoglycemia in Type 1 Diabetes are Preceded, and Followed, within 48 Hours by Measurable Disturbances in Blood Glucose. *J of Clinical Endocrinology and Metabolism*, 85: 4287-4292.

10. Kovatchev B P & Cox D J (2001). Method, system, and computer program product for the evaluation of glycemic control in diabetes from self-monitoring data, PCT/US01/09884; *World Intellectual Property Organization*, No. WO 01/72208.

11. Kovatchev B P & Cox D J (2003). Method, system, and computer program product for processing of self-monitoring blood glucose (SMBG) data to enhance diabetic self-management, PCT/US2003/25053; *World Intellectual Property Organization, No. WO* 2004/015539.

12. Kovatchev B P, Cox D J, Gonder-Frederick L A and W L Clarke (2002). Methods for quantifying self-monitoring blood glucose profiles exemplified by an examination of blood glucose patterns in patients with Type 1 and Type 2 Diabetes. *Diabetes Technology and Therapeutics*, 4 (3): 295-303.

13. Kovatchev B P, Cox D J, Gonder-Frederick L A and W L Clarke. Symmetrization of the blood glucose measurement scale and its applications. *Diabetes Care* 20: 1655-1658, 1997

14. Kovatchev B P, Cox D J, Gonder-Frederick L A Young-Hyman D, Schlundt D and W L Clarke (1998). Assessment of Risk for Severe Hypoglycemia Among Adults with IDDM: Validation of the Low Blood Glucose Index, *Diabetes Care*, 21: 1870-1875.

15. Kovatchev B P, Cox D J, Kumar A, Gonder-Frederick L A, Clarke W L (2003). Algorithmic Evaluation of Metabolic Control and Risk of Severe Hypoglycemia in Type 1 and Type 2 Diabetes Using Self-Monitoring Blood Glucose (SMBG) Data. *Diabetes Technology and Therapeutics*, 5 (5): 817-828.

16. Kovatchev B P, Otto E, Cox D J, Gonder-Frederick L A, Clarke W L. Evaluation of a New Measure of Blood Glucose Variability in Diabetes. *Diabetes Care*, 29: 2433-2438, 2006.

17. Kovatchev B P. Method, system, and computer program product for evaluation of blood glucose variability in diabetes from self-monitoring data; PCT/US2007/000370; 2007.

18. Kovatchev B P, Straume M, Cox D J, Farhy L S. Risk analysis of blood glucose data: A quantitative approach to optimizing the control of insulin dependent diabetes. *J of Theoretical Medicine*, 3:1-10, 2001.

19. Ryan E A, Shandro T, Green K, Paty B W, Senior P A, Bigam D, Shapiro A M J, Vantyghem M C. Assessment of the Severity of Hypoglycemia and Glycemic Lability in Type 1 Diabetic Subjects Undergoing Islet Transplantation *Diabetes* 53: 955-962, 2004

20. Santiago J V. Lessons from the Diabetes Control and Complications Trial, *Diabetes*, 42:1549-1554, 1993

21. Schlichtkrull J, Munck O, Jersild M. The M-value, an index of blood glucose control in diabetics. *Acta Med Scand* 177: 95-102, 1965

22. Segel S A, Paramore D S, Cryer P E. Hypoglycemia-associated autonomic failure in advanced type 2 diabetes. *Diabetes* 51: 724-733, 2002

23. Service F J, Molner G D, Rosevear J W, Ackerman E, Gatewood L C, Taylor W F. Mean amplitude of glycemic excursions, a measure of diabetic instability *Diabetes* 19: 644-655, 1970

24. The Diabetes Control and Complications Trial Research Group. Hypoglycemia in the Diabetes Control and Complications Trial. *Diabetes* 46: 271-286, 1997

25. The Diabetes Control and Complications Trial Research Group. The effect of intensive treatment of diabetes on the development and progression of long-term complications of insulin-dependent diabetes mellitus. *N Engl J Med* 329: 978-986, 1993

26. The Diabetes Control and Complications Trial Research Group: The relationship of glycemic exposure (HbA1c) to the risk of development and progression of retinopathy in the Diabetes Control and Complications Trial. *Diabetes* 44:968-983, 1995

27. UK Prospective Diabetes Study Group (UKPDS). Intensive blood-glucose control with sulphonylureas or insulin compared with conventional treatment and risk of complications in patients with type 2 diabetes. *Lancet* 352: 837-853, 1998.

Further, the devices, systems, compositions, computer program products, and methods of various embodiments of the invention disclosed herein may utilize aspects disclosed in the following references, applications, publications and patents and which are hereby incorporated by reference herein in their entirety:

a. PCT/US2008/082063, entitled "Model Predictive Control Based Method for Closed-Loop Control of Insulin Delivery in Diabetes Using Continuous Glucose Sensing", filed Oct. 31, 2008 b. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data" filed Jul. 8, 2008 claiming priority to 60/958,767 filed Jul. 9, 2007.

c. PCT/US2008/067725, entitled "Method, System and Computer Simulation Environment for Testing of Monitoring and Control Strategies in Diabetes," filed Jun. 20, 2008;

d. PCT/US2008/067723, entitled "LQG Artificial Pancreas Control System and Related Method.".

e. PCT/US2007/085588 not yet published filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes."

f. U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes.".

g. PCT International Application Serial No. PCT/US2005/013792, filed Apr. 21, 2005, entitled "Method, System, and Computer Program Product for Evaluation of the Accuracy of Blood Glucose Monitoring Sensors/Devices;"

h. U.S. patent application Ser. No. 11/578,831, filed Oct. 18, 2006 entitled "Method, System and Computer Program Product for Evaluating the Accuracy of Blood Glucose Monitoring Sensors/Devices;"

i. PCT International Application Serial No. PCT/US01/09884, filed Mar. 29, 2001, entitled "Method, System, and Computer Program Product for Evaluation of Glycemic Control in Diabetes Self-Monitoring Data;"

j. U.S. Pat. No. 7,025,425 B2 issued Apr. 11, 2006, entitled "Method, System, and Computer Program Product for the Evaluation of Glycemic Control in Diabetes from Self-Monitoring Data;"

k. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);

l. PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"

m. PCT International Application Serial No. PCT/US2003/025053 filed Aug. 8, 2003; and U.S. patent application Ser. No. 10/524,094 filed Feb. 9, 2005 entitled "Managing and Processing Self-Monitoring Blood Glucose" (Publication No. 2005/214892);

n. PCT International Application Serial No PCT/US2006/033724, filed Aug. 29, 2006, entitled "Method for Improvising Accuracy of Continuous Glucose Sensors and a Continuous Glucose Sensor Using the Same;"

o. PCT International Application No. PCT/US2007/000370, filed Jan. 5, 2007, entitled "Method, System and Computer Program Product for Evaluation of Blood Glucose Variability in Diabetes from Self-Monitoring Data;"

p. PCT International Patent Application No. PCT/US2007/082744, filed Oct. 26, 2007, entitled "For Method, System and Computer Program Product for Real-Time Detection of Sensitivity Decline in Analyte Sensors" and U.S. patent application Ser. No. 11/925,689, filed Oct. 26, 2007, entitled "For Method, System and Computer Program Product for Real-Time Detection of Sensitivity Decline in Analyte Sensors;"

q. PCT International Application No. PCT/US00/22886, filed Aug. 21, 2000, entitled "Method and Apparatus for Predicting the Risk of Hypoglycemia;"

8. U.S. Pat. No. 6,923,763 B1, issued Aug. 2, 2005, entitled "Method and Apparatus for Predicting the Risk of Hypoglycemia."

APPENDIX A

Methodology: Tracking of the Probability for Hypoglycemia from SMBG

Overview:

As formulated in the original research proposal, one of the goals of this study was to develop an algorithm forecasting risk for hypoglycemia in terms of a probability of a hypoglycemic event within a pre-specified time frame.[1] An approach may use, for example, all previously accumulated data and referred to certain components of the previously developed Algorithms 2, 3, and 4, specifically the Low Blood Glucose Index (LBGI) and the Average Daily Risk Range (ADRR). The available data was split into a training and test data sets. Training data was used for development of the algorithm, after which all algorithm parameters were fixed. Then, independent testing was performed using the test data, which ensured the credibility of the results.

[1] Another goal was to develop a glucose variability tracking system, which has been accomplished and reported to Lifescan previously.

Thus, an exemplary overall deliverable from this study is a risk-tracking method that, similarly to a weather forecast, projects the probability for hypoglycemia in the next few days using past ADRR and LBGIS patterns. The risk tracking method was specifically optimized to determine the optimal formula achieving prediction of 51% of hypoglycemic episodes below 50 mg/dl, 24 hours ahead. A number of scenarios were then reviewed, including analysis of the influence of SMBG frequency, subject population analysis of the frequency of hypoglycemia predictions, and analysis of the influence of the duration of the prediction period (e.g. 24 vs. 48 hours). The description of the data and the results are included in the following pages:

Data:

Two data sets from past studies were selected for training and test data set:

Training data included a data set provided by Lifescan containing SMBG data for N=222 subjects with Type 1 and diabetes derived from a SMBG user database. These subjects were monitored with SMBG for up to 4 months. The 222 subjects included in the training data were those who: (i) had at least 30 days of SMBG, and (ii) had at least 2 SMBG readings per day on average (e.g. someone with 60 readings over 30 days would be included, even if all readings are concentrated in one week). The demographic characteristics of these subjects are presented in Table 1.

Test data included data collected at UVA during the Lifescan Phase 2 study containing SMBG data for N=179 subjects with Type 1 (N=91) and Type 2 diabetes (N=88) who were monitored with SMBG for 4-6 months. Similarly to the training data, these subjects met the two conditions: (i) had at least 30 days of SMBG, and (ii) had at least 2 SMBG readings per day on average. Their demographic characteristics are presented in Table 1.

In addition to demographic and biometric characteristics, Table 1 includes a number of study parameters, including the average duration of study, the SMBG frequency during the study, as well as key SMBG parameters, such as average BG, percent readings below 70 mg/dl and 50 mg/dl, LBGI, and ADRR.

The ADRR computed from the SMBG readings in the preceding 14 days. Several cutoff points for the LBGI and the ADRR were investigated. The probabilities for hypoglycemia <=50 mg/dl increased uniformly with the increase of both the LBGI and the ADRR cutoff values. Finally, it was decided that a cutoff of LBGI≥3.5 and ADRR≥30 appears to be optimal, bringing the percentage of predicted hypoglycemic episodes to 50% with a minimum number of inaccurate flags, i.e. minimum number of occasions when hypoglycemia was predicted, but an episode was not encountered.

In an embodiment, the algorithm can have one of two modes of operation:

Mode 1—Sliding window: At every SMBG reading the algorithm evaluates the risk (probability) for hypoglycemia in the next 24 hours and presents the results to the patient.

Mode 2—Daily cycle: Every evening, after all SMBG data for the day are collected (e.g. at the last SMBG for the day) the algorithm evaluates the risk (probability) for hypoglycemia in the next 24 hours and presents the results to the patient;

It is expected that a meter implementation can have either of these two modes of use. We need to keep in mind, however, that if Mode 1 is used the ADRR cannot be updated at each reading (because it is daily risk range) and therefore only changes in the LBGI could be used to update the prediction at each reading. To avoid confusion and to operate with non-overlapping time windows, in the testing below we use Mode 2 of Algorithm 7.

A possible implementation combining Modes 1 and 2 would be the methodology or algorithm to issue a warning for hypoglycemia in the next 24 hours close to the last reading of the day, i.e. after certain fixed time in the evening. If this is known in advance to the patient, the patient will be prompted to measure at bedtime, which is quite beneficial for getting a good daily profile. The time threshold (e.g. 9 PM) can be user-selected.

TABLE 1

|  | Training Data (N = 222 subjects with T1DM) | Test Data (N = 91 subjects with T1DM and N = 88 subjects with T2DM) | |
| --- | --- | --- | --- |
|  |  | T1DM | T2DM |
| Age (years) | 32.3 (SD = 17.6) | 40.4 (SD = 11.2) | 50.6 (SD = 8.2) |
| Gender (% male) | 46.0% | 44.9% | 42.1% |
| BMI | 24.0 (SD = 4.8) | 25.6 (SD = 4.5) | 35.4 (SD = 8.9) |
| Baseline HbA1c | 8.1 (SD = 1.2) | 7.6 (SD = 1.25) | 8.5 (SD = 2.0) |
| Years of diabetes | 15.4 (SD = 12.2) | 19.7 (SD = 10.9) | 11.4 (SD = 8.4) |
| Duration of study (days) | 80.5 (SD = 28.3) | 200.5 (57.0) | 116.3 (27.3) |
| SMBG frequency (readings/day) | 4.4 (SD = 1.9) | 5.0 (SD = 2.0) | 3.4 (SD = 0.66) |
| Average BG | 190.3 (SD = 40.4) | 170.7 (SD = 36.9) | 178.5 (SD = 49.9) |
| LBGI | 2.42 (SD = 2.1) | 2.91 (SD = 2.35) | 0.75 (SD = 1.1) |
| Readings <= 70 mg/dl | 10.8% | 12.9% | 4.0% |
| Readings <= 50 mg/dl | 3.7% | 4.4% | 2.1% |
| ADRR | 42.1 (SD = 13.9) | 37.8 (SD = 11.6) | 22.8 (SD = 13.5) |

Brief Description of Methodology or Algorithm 7

The training data set was used to develop and algorithm using the Low BG Index (LBGI) and the Average Daily Risk Range (ADRR) to estimate the probability for hypoglycemia in the next 24 hours. Other variables were considered for inclusion in the algorithm, but were rejected upon examination. The final algorithm used the SMBG data to compute:

The LBGI computed from the SMBG readings in the preceding 48 hours, and

All parameters of Algorithm 7 were optimized using training data and then fixed. In the following pages we present the results from the testing of methodology or Algorithm 7 on the independent Test Data Set.

Results

Data Restrictions: We re-emphasize that in an embodiment the only requirement for a subject to be included in the test data set was to have a certain number of SMBG readings amounting to an average of readings/day during the study. This is similar to minimum-data criteria that were previously used in other algorithms. Because this criterion does not imply that we would have 2 or more readings every day, various testing frequency situations are investigated below. In addition:

No restrictions were imposed on the number of readings used to compute the LBGI—even one reading in a day would generate prediction for the next day;

ADRR was computed only on days that have 3 or more SMBG readings, but the number of days with 3 or more readings during the preceding 14 days is not restricted. For example, if only one out of 14 days includes ≥3 SMBG readings, the ADRR is computed and the results are included in the tables below.

Overall Results:

The total number of days of observation in this data set was 30,757 of which 28,480 had at least one SMBG reading. These 28,480 days included 18,247 days of observation in T1DM and 10,233 days of observation in T2DM. The number of days with hypoglycemic episodes <=50 mg/dl recorded during the study was 3,148 (2,974 in T1DM and 174 in T2DM), which amounts to overall baseline frequency of days with hypoglycemia <=50 mg/dl of 10.2% (or 11.1% if only days with SMBG are used; 16.3% in T1DM and 1.7% in T2DM). Table 2 presents the results obtained in this data set without any restrictions on testing frequency.

TABLE 2

PREDICTION OF HYPOGLYCEMIA

| | |
|---|---|
| Percent of all hypoglycemic episodes <=50 mg/dl predicted by the algorithm within 24 hours from "raising a hypoglycemia flag" | 52.8% |
| Percent inaccurate flags (hypoglycemia predicted, but no episode occurring) | 10.6% |
| Percent of total flagged days | 15.9% |
| Likelihood of hypoglycemia <=50 mg/dl on the day after the flag is raised | 33.3% |

The bold numbers in Table 2 reflect the optimization criteria used in the analysis of training data. It is evident that in the test data set the percent predicted hypoglycemic episodes holds above 50%, and is even slightly better than the training data. This is accompanied by 10.6% of days when a flag would be raised inappropriately and by 15.9% of total days with flag raised. In other words, a flag would be raised once a week on average, and inappropriate flag would be raised once in 10 days. The likelihood for hypoglycemia <=50 mg/dl is 33.3% after a flag is raised, which is 3-fold higher than the baseline frequency.

Testing Frequency Analysis:

Table 3 presents the dependence of the accuracy of prediction on the frequency of testing. This is done by raising the flag only on days that have a minimum of 2, 3, 4, 5, or 6 SMBG readings. The assumption is that if there is appropriate number of readings, there is a flag (or indication of no flag) for the next day. If there is insufficient number of readings, no prediction can be made either way and the algorithm remains silent (or says not enough readings). Thus, the hypoglycemic episodes that might occur after a day with insufficient readings are not counted as prediction or false alarm. The rows in Table 3 are the same as in Table 2; the last line presents the number and percent of days that satisfy the number-of-readings requirement (e.g. if the restriction is imposed, the algorithm will remain silent in (100-this percentage) of days.

TABLE 3

| | Minimum Number Of Readings to Calculate a Flag for the Next Day | | | | |
|---|---|---|---|---|---|
| | ≥2 | ≥3 | ≥4 | ≥5 | ≥6 |
| % hypoglycemia predicted | 53.2 | 54.0 | 57.1 | 63.2 | 71.5 |
| % inaccurate flags | 10.3 | 9.6 | 8.5 | 6.3 | 3.0 |
| % total flagged days | 15.6 | 14.7 | 13.0 | 9.9 | 5.3 |
| Likelihood for hypoglycemia on the next day | 33.7 | 34.4 | 34.9 | 36.6 | 42.7 |
| Percent days meeting the condition | 27,181 (95.4%) | 24,335 (85.4%) | 19,080 (67.0%) | 9,595 (33.7%) | 4,052 (14.2%) |

It is evident that, while testing frequency improves the prediction, most improvement occurs at quite high (and therefore unrealistic) testing frequencies. We can say, however, that "if you test 3 times every day, you'll get 54% of all days with episodes <=50 flagged 24 hours in advance, with less than 10% of days including inaccurate flags.

Flagging Rate Analysis:

Table 4 presents the percent of subjects in several flagging rate categories, beginning with 0 flags throughout the study to above 50% of days flagged. We also include the average % of days with hypoglycemia <=50 mg/dl for each flagging category. It is evident that higher flagging rate is related to higher frequency of hypoglycemic episodes:

TABLE 4

| | | Percent Days Flagged | | | | | |
|---|---|---|---|---|---|---|---|
| | | 0 | 0<-5% | 5-10% | 10-30% | 30-50% | ≥50% |
| All Subjects | Number of subjects | 84 | 23 | 14 | 25 | 17 | 16 |
| | % subjects | 46.9% | 12.8% | 7.8% | 14.0% | 9.5% | 8.9% |
| | % days with hypo | 0.6% | 2.2% | 4.6% | 10.8% | 23.2% | 42.9% |
| T1DM | Number of subjects | 9 | 15 | 13 | 22 | 17 | 15 |
| | % subjects | 9.9% | 16.5% | 14.3% | 24.2% | 18.7% | 16.5% |
| | % days with hypo | 0.6% | 2.4% | 4.8% | 10.4% | 23.2% | 43.7% |
| T2DM | Number of subjects | 75 | 8 | 1 | 3 | 0 | 1 |
| | % subjects | 85.2% | 9.1% | 1.1% | 3.4% | 0.0% | 1.1% |
| | % days with hypo | 0.6% | 1.5% | 2.1% | 15.3% | 0 | 24.6% |

From Table 4 we can conclude that people who get frequent flags have indeed high rate of hypoglycemia, comparable to flag frequency. Thus, if the flag works as intended and prompts appropriate corrective actions, the frequency of hypoglycemia should go down, and the frequency of flagging should go down as well.

Personalized Flagging Thresholds:

In addition, we could consider setting different thresholds for subjects at different frequency of hypoglycemia, e.g. we could use the LBGI or the frequency of SMBG below certain threshold to adjust automatically the flag raising thresholds every two weeks. Alternatively (and this is probably the better option) a threshold could be preset by the subject, i.e. a person could decide to limit the frequency of flagging to a certain percentage of days, which would automatically shift the ADRR/LBGI thresholds for flagging to higher values.

Table 5a presents such a scenario for all subjects in the test data set, gradually increasing the thresholds for ADRR and LBGI from their current values of 30 and 3.5 (in Table 2). Such an increase could be automatic, depending on observed frequency of flagging, or user-initiated by patient choice.

entirely accounted for by the frequency of low BG episodes. More precisely, the correlation of testing frequency with the percentage of BG readings below 70 mg/dl was similar R=0.4, p<0.01.

To assess the relative importance of testing frequency and occurrence of hypoglycemia for flagging, we perform a linear regression with flag frequency as the dependent variable and testing frequency, BGs<=70 mg/dl and BGs<=50 mg/dl as predictors. The regression shows that the percentages of low BG readings are the primary predictors of flag frequency, explaining over 80% of the variance of flagging frequency (R-square=81%). When added to the equation, testing frequency increases R-square to 82%, i.e. explains less than 1% of the frequency of flagging and is not significant.

Thus, an important conclusion can be made: While, superficially, flagging frequency is correlated with the fre- TABLE 5a

| Whole population | Gradually Increasing ADRR and LBGI Thresholds | | | | |
| --- | --- | --- | --- | --- | --- |
| | ADRR ≥ 30 LBGI ≥ 3.5 | ADRR ≥ 35 LBGI ≥ 3.5 | ADRR ≥ 40 LBGI ≥ 4.0 | ADRR ≥ 45 LBGI ≥ 4.5 | ADRR ≥ 50 LBGI ≥ 5.0 |
| % hypoglycemia predicted | 52.8% | 43.5% | 29.9% | 21.8% | 16.2% |
| % inaccurate flags | 10.6% | 8.1% | 4.8% | 2.8% | 1.7% |
| % total flagged days | 15.9% | 12.5% | 7.8% | 5% | 3.3% |
| Likelihood for hypoglycemia on the next day | 33.3% | 35.0% | 38.6% | 43.8% | 49.0% |

Table 5b presents gradual increase of the ADRR and LBGI threshold in subjects who were in the top 25% flagging rate with the preset thresholds of 30 and 3.5. It is evident that for these subjects the flagging rate can be significantly decreased with threshold increase. Because baseline prediction of hypoglycemia in these subjects is better, a certain decrease in flagging rate can be done without compromising the prediction probability to below 50%.

quency of testing, more frequent testing is entirely driven by more frequent hypoglycemia. Naturally, by algorithm design, more frequent hypoglycemia would result in more frequent flagging. Therefore flagging frequency is not directly related to frequency of testing. Any apparent relationship is mediated and entirely determined by the frequency of hypoglycemic episodes.

TABLE 5b

| Ss at top 25% flag frequency | Gradually Increasing ADRR and LBGI Thresholds | | | | |
| --- | --- | --- | --- | --- | --- |
| | ADRR ≥ 30 LBGI ≥ 3.5 | ADRR ≥ 35 LBGI ≥ 3.5 | ADRR ≥ 40 LBGI ≥ 4.0 | ADRR ≥ 45 LBGI ≥ 4.5 | ADRR ≥ 50 LBGI ≥ 5.0 |
| % hypoglycemia predicted | 62.0% | 51.9% | 36.1% | 26.3% | 19.6% |
| % inaccurate flags | 27.9% | 22.8% | 14.2% | 8.4% | 5.2% |
| % total flagged days | 44.6% | 36.7% | 23.9% | 15.5% | 10.5% |
| Likelihood for hypoglycemia on the next day | 37.3% | 38.0% | 40.6% | 45.5% | 50.2% |

Correlation between Testing Frequency and Flagging Rate

For each subject in the test data set we compute the following variables:
Frequency of raised flags per day of study;
Average number of SMBG readings per day;
Percent of readings <=70 mg/dl and percent readings <=50 mg/dl.
The correlation between testing and flag frequency was positive: R=0.45, p<0.01. However, this correlation was Analysis of 48-hour Prediction Horizon:

We now go back to the previously preset ADRR/LBGI thresholds of 30 and 3.5 and investigate the influence on the prediction horizon. Specifically, we increase the prediction horizon from 24 to 48 hours ahead. Table 6 presented results analogous to Table 2 in the case of 48-hour prediction. It is clear that, while the percentage of flag raising remains the same, all other numbers are favorably influenced. In particular, the prediction rate increases by 10% and the likelihood for subsequent hypoglycemia within the subsequent 48 hours is significantly improved:

TABLE 6

PREDICTION OF HYPOGLYCEMIA

| | |
|---|---|
| Percent of all hypoglycemic episodes <=50 mg/dl predicted by the algorithm within 48 hours from "raising a hypoglycemia flag" | 62.3% |
| Percent inaccurate flags (hypoglycemia predicted, but no episode occurring) | 8.6% |
| Percent of total flagged days | 15.9% |
| Likelihood of hypoglycemia <=50 mg/dl on the day after the flag is raised | 49.9% |

Analysis of BG Prediction Target of 70 mg/dl:

Finally, we redefine the prediction target from 50 mg/dl to 70 mg/dl to see what would be the rate of prediction of mild hypoglycemia. Doing so we have two options for flagging:

First, we can use the exact settings of the flag that were used for prediction of 50 mg/dl above. Table 7a presents these results for both 24- and 48-hour prediction horizons. The overall number of days with hypoglycemic episodes <=70 mg/dl recorded during the study was 7,569 (7,569 in T1DM and 891 in T2DM), which amounts to overall baseline frequency of days with hypoglycemia <=70 mg/dl of 29.7% (41.5% in T1DM and 8.7% in T2DM). Thus, following a flag the likelihood for hypoglycemia <=70 mg/dl essentially doubles.

TABLE 7a

PREDICTION OF HYPOGLYCEMIA

| | 24 h horizon | 48 h horizon |
|---|---|---|
| Percent of all hypoglycemic episodes <=70 mg/dl predicted by the algorithm. | 35.8% | 44.7% |
| Percent inaccurate flags (hypoglycemia predicted, but no episode occurring) | 6.6% | 3.6% |
| Percent of total flagged days | 15.9% | 15.9% |
| Likelihood of hypoglycemia <=50 mg/dl on the day after the flag is raised | 61.8% | 78.8% |

Second, using training data we optimize the ADRR and LBGI threshold to specifically predict BG<=70 mg/dl, which leads to the thresholds ADRR>20 and LBGI>2.5. As seen in Table 7b, with this specific optimization the % predicted hypoglycemia rises above 50%, with quite low rate of inaccurate flagging and likelihood for subsequent hypoglycemia approaching 60% within 24 hours and 75% within 48 hours.

TABLE 7b

PREDICTION OF HYPOGLYCEMIA

| | 24 h horizon | 48 h horizon |
|---|---|---|
| Percent of all hypoglycemic episodes <=70 mg/dl predicted by the algorithm. | 52% | 62.0% |
| Percent inaccurate flags (hypoglycemia predicted, but no episode occurring) | 11.7% | 6.8% |
| Percent of total flagged days | 27.1% | 27.1% |
| Likelihood of hypoglycemia <=50 mg/dl on the day after the flag is raised | 57% | 75.1% |

SUMMARY

The proposed method provides, but not limited thereto, an embodiment for tracking the probability of hypoglycemia from SMBG has been developed on a large training data set containing SMBG data for 222 individuals with T1DM and was then tested in an independent test data set of N=179 individuals: N=91 with T1DM and N=88 with T2DM (Table 1). Out of many considered variables, the LBGI and the ADRR appear to be the best combination for predicting of hypoglycemic episodes. Various combinations of cutoffs for the LBGI and ADRR were investigated, leading to the optimal cutoff of LBG>=3.5 and ADRR>=30, which achieved prediction of over 50% of hypoglycemic episodes below 50 mg/dl in the subsequent 24 hours (Table 2), i.e. over half of hypoglycemic episodes below 50 mg/dl are "flagged" up to 24 hours in advance.

In addition:

The precision of hypoglycemia prediction increases with testing frequency (Table 3);

Most subjects with T2DM and some subjects with T1DM who rarely experience hypoglycemia would never get a flag (Table 4);

In general, the flagging frequency is almost entirely predetermined by the frequency of hypoglycemic episodes, and is not dependent on the frequency of testing;

For people with very high rates of hypoglycemia the flagging frequency can be reduced automatically, or by the user (Tables 5A and 5B);

The prediction horizon can be increased from 24 to 48 hours, which would improve the results substantially (Table 6);

Hypoglycemic episodes <=70 mg/dl are reasonably well predicted by the algorithm without changing its parameters (Table 7A), or the prediction can be optimized for this specific BG target (Table 7B).

What is claimed is:

1. A method for maintaining the health of a diabetic patient by preventing the occurrence of a hypoglycemic event in said patient, comprising:

obtaining self monitoring blood glucose (SMBG) readings from the patient;

measuring glycemic variability of said patient and low blood glucose (BG) of said patient based on said obtained SMBG readings;

creating in a processor a bivariate distribution that maps probability for an upcoming hypoglycemic event in said patient jointly to values of said measured glycemic variability and said measured low blood glucose (BG);

optimizing in said processor the bivariate distribution to achieve prediction of a predetermined percentage of hypoglycemic events below a predetermined BG value occurring in said patient within a predetermined future time period;

tracking in said processor the optimized distribution over time using routine SMBG readings from the patient;

outputting via said processor a message to said patient when said optimized distribution indicates a certain probability for the occurrence of a hypoglycemic event in said patient within said predetermined future time period, based on SMBG data obtained from said patient; and causing said patient to take a physical action in response to receiving said message to prevent a hypoglycemic event from occurring in said patient.

2. The method of claim 1, wherein the function measuring glycemic variability is Average Daily Risk Range (ADRR).

3. The method of claim 2, wherein $$ADRR = \frac{1}{M}\sum_{i=1}^{M}[LR^i + HR^i]$$

$LR^i = \max(rl(x_1^i), rl(x_2^i), \ldots, rl(x_n^i))$ and $HR^i = \max(rh(x_1^i), rh(x_2^i), \ldots, rh(x_n^i))$ for day#i; i=1, 2, ... M;

$x_1^M, x_2^M, \ldots, x_n^M$ are a series of $n^M$ SMBG readings (BG) taken on Day M;

$rl(BG) = r(BG)$ if $f(BG) < 0$ and 0 otherwise;

$rh(BG) = r(BG)$ if $f(BG) > 0$ and 0 otherwise;

$r(BG) = 10f(BG)^2$;

$f(BG,\alpha,\beta) = [(\ln(BG))^\alpha - \beta], \alpha, \beta > 0$.

4. The method of claim 1, wherein the function measuring low blood glucose is Low Blood Glucose Index (LBGI).

5. The method of claim 4, wherein $$LBGI = \frac{1}{(n^{M-1} + n^M)}\left[\sum_{s=1}^{n^{M-1}} rl(x_s^{M-1}) + \sum_{t=1}^{n^M} rl(x_t^M)\right]$$

$x_1^M, x_2^M, \ldots, x_n^M$ are a series of $n^M$ SMBG readings (BG) taken on Day M:

$rl(BG) = r(BG)$ if $f(BG) < 0$ and 0 otherwise;

$r(BG) = 10f(BG)^2$;

$f(BG,\alpha,\beta) = [(\ln(BG))^\alpha - \beta], \alpha, \beta > 0$.

6. The method of claim 1, wherein said optimizing comprises determining threshold values of said functions that are effective to predict a predefined minimum percentage of all occurrences of hypoglycemic events in said patient.

7. The method of claim 6, wherein said percentage is 50%.

8. The method of claim 6, wherein a hypoglycemic event is determined to be BG ≤ 50 mg/dl.

9. The method of claim 6, wherein said predetermined future time period is a succeeding 24 hour time period.

10. The method of claim 3, wherein the function measuring low blood glucose is Low Blood Glucose Index (LBGI).

11. The method of claim 10, wherein $$LBGI = \frac{1}{(n^{M-1} + n^M)}\left[\sum_{s=1}^{n^{M-1}} rl(x_s^{M-1}) + \sum_{t=1}^{n^M} rl(x_t^M)\right]$$

$x_1^M, x_2^M, \ldots x_n^M$ are a series of $n^M$ SMBG readings (BG) taken on Day M;

$rl(BG) = r(BG)$ if $f(BG) < 0$ and 0 otherwise;

$r(BG) = 10f(BG)^2$;

$f(BG,\alpha,\beta) = [(\ln(BG))^\alpha - \beta], \alpha, \beta > 0$.

12. The method of claim 11, wherein the probability P for upcoming hypoglycemia is given by $$P(Hypo \mid ADRR > x \text{ \& } LBGI > y) = a(y) + (100 - a(y))\frac{\left(\frac{x}{b(y)}\right)^{c(y)}}{1 + \left(\frac{x}{b(y)}\right)^{c(y)}}$$

$a(y) = \alpha_a + \beta_a y$ $b(y) = \alpha_b + \beta_b y$ $$c(y) = \alpha_c + \beta_c \frac{\left(\frac{y}{\delta_c}\right)^{\gamma_c}}{1 + \left(\frac{y}{\delta_c}\right)^{\gamma_c}}.$$

13. The method of claim 12, wherein $\alpha_a = 15.1$ range: [5,20]

$\beta_a = 3.13$ range: [1,5]

$\alpha_b = 116$ range: [50,150]

$\beta_b = -5.66$ range: [-10,0]

$\alpha_c = 2.9$ range: [1,5]

$\beta_c = 1$ range: [1,5]

$\delta_c = 2.35$ range: [1,10]

$\gamma_c = 3.76$ range: [1,5]

14. The method of claim 13, wherein said mapping is based on results of a training data set obtained from a population of subjects having Type 1 diabetes.

15. The method of claim 14, wherein said mapping maps coordinate pairs of {LBGI, ADRR} to the probability for hypoglycemia, defined as BG ≤50 mg/dl, in the subsequent 24 hours.

16. The method of claim 15, wherein LBGI is computed from SMBG readings in the preceding 48 hours.

17. The method of claim 16, wherein ADRR is computed from SMBG readings in the preceding 14 days.

18. The method of claim 17, wherein the presence of a flag triggers outputting of said message, and wherein $$\text{flag} = \begin{cases} 1 & \text{if } ADRR > x \text{ \& } LBGI > y \\ 0 & \text{otherwise} \end{cases}$$

Where x and y are predefined values.

19. A system for maintaining the health of a diabetic patient by preventing the occurrence of a hypoglycemic event in said patient, comprising:
- a processor configured to obtain self monitoring blood glucose (SMBG) readings from the patient and to measure glycemic variability of said patient and low blood glucose (BG) of said patient based on said obtained SMBG readings;
- a storage medium;
- a bivariate distribution stored in said storage medium, which maps probability for an upcoming hypoglycemic event in said patient jointly to values of said measured glycemic variability and said measured low blood glucose (BG), wherein said bivariate distribution allows said processor to predict a predetermined percentage of hypoglycemic events below a predetermined BG value occurring in said patient within a predetermined future time period;

said processor being configured to optimize said bivariate distribution and to track the optimized distribution over time using routine SMBG readings received from the patient;

said processor being configured to output a message to said patient when said optimized distribution indicates a certain probability for the occurrence of a hypoglycemic event in said patient within said predetermined future time period, based on SMBG data obtained from said patient; and in response to receiving said message said patient is caused to take a physical action to prevent a hypoglycemic event from occurring in said patient.

20. The system of claim 19, wherein the function measuring glycemic variability is Average Daily Risk Range (ADRR).

21. The system of claim 20, wherein $$ADRR = \frac{1}{M}\sum_{i=1}^{M}[LR^i + HR^i]$$

$LR^i = \max(rl(x_1^i), rl(x_2^i), \ldots, rl(x_n^i))$ and $HR^i = \max(rh(x_1^i), rh(x_2^i), \ldots, rh(x_n^i))$ for day#i; i=1, 2, ... M;

$x_1^M, x_2^M, \ldots x_n^M$ are a series of $n^M$ SMBG readings (BG) taken on Day M;

$rl(BG) = r(BG)$ if $f(BG) < 0$ and 0 otherwise;

$rh(BG) = r(BG)$ if $f(BG) > 0$ and 0 otherwise;

$r(BG) = 10 f(BG)^2$;

$f(BG, \alpha, \beta) = [(\ln(BG))^\alpha - \beta], \alpha, \beta > 0$.

22. The system of claim 19, wherein the function measuring low blood glucose is Low Blood Glucose Index (LBGI).

23. The system of claim 22, wherein $$LBGI = \frac{1}{(n^{M-1} + n^M)}\left[\sum_{s=1}^{n^{M-1}} rl(x_s^{M-1}) + \sum_{t=1}^{n^M} rl(x_t^M)\right]$$

$x_1^M, x_2^M, \ldots, x_n^M$ are a series of $n^M$ SMBG readings (BG) taken on Day M;

$rl(BG) = r(BG)$ if $f(BG) < 0$ and 0 otherwise;

$r(BG) = 10 f(BG)^2$;

$f(BG, \alpha, \beta) = [(\ln(BG))^\alpha - \beta], \alpha, \beta > 0$.

24. The system of claim 19, wherein said optimizing comprises determining threshold values of said functions that are effective to predict a predefined minimum percentage of all occurrences of hypoglycemic events in said patient.

25. The system of claim 24, wherein said percentage is 50%.

26. The system of claim 24, wherein a hypoglycemic event is determined to be BG ≤50 mg/dl.

27. The system of claim 24, wherein said predetermined future time period is a succeeding 24 hour time period.

28. The system of claim 21, wherein the function measuring low blood glucose is Low Blood Glucose Index (LBGI).

29. The system of claim 28, wherein $$LBGI = \frac{1}{(n^{M-1} + n^M)}\left[\sum_{s=1}^{n^{M-1}} rl(x_s^{M-1}) + \sum_{t=1}^{n^M} rl(x_t^M)\right]$$

$x_1^M, x_2^M, \ldots x_n^M$ are a series of $n^M$ SMBG readings (BG) taken on Day M;

$rl(BG) = r(BG)$ if $f(BG) < 0$ and 0 otherwise;

$r(BG) = 10 f(BG)^2$;

$f(BG, \alpha, \beta) = [(\ln(BG))^\alpha - \beta], \alpha, \beta > 0$.

30. The system of claim 29, wherein the probability P for upcoming hypoglycemia is given by $$P(Hypo \mid ADRR > x \;\&\; LBGI > y) = a(y) + (100 - a(y))\frac{\left(\frac{x}{b(y)}\right)^{c(y)}}{1 + \left(\frac{x}{b(y)}\right)^{c(y)}}$$

$a(y) = \alpha_a + \beta_a y$ $b(y) = \alpha_b + \beta_b y$ $c(y) = \alpha_c + \beta_c \frac{\left(\frac{y}{\delta_c}\right)^{\gamma_c}}{1 + \left(\frac{y}{\delta_c}\right)^{\gamma_c}}$.

31. The system of claim 30, wherein $\alpha_a = 15.1$ range: [5,20]

$\beta_a = 3.13$ range: [1,5]

$\alpha_b = 116$ range: [50,150]

$\beta_b = -5.66$ range: [-10,0]

$\alpha_c = 2.9$ range: [1,5]

$\beta_c = 1$ range: [1,5]

$\delta_c = 2.35$ range: [1,10]

$\gamma_c = 3.76$ range: [1,5]

32. The system of claim 31, wherein said mapping is based on results of a training data set obtained from a population of subjects having Type 1 diabetes.

33. The system of claim 32, wherein said mapping maps coordinate pairs of {LBGI, ADRR} to the probability for hypoglycemia, defined as BG ≤ 50 mg/dl, in the subsequent 24 hours.

34. The system of claim 33, wherein LBGI is computed from SMBG readings in the preceding 48 hours.

35. The system of claim 34, wherein ADRR is computed from SMBG readings in the preceding 14 days.

36. The system of claim 35, wherein the presence of a flag triggers outputting of said message, and wherein $$\text{flag} = \begin{cases} 1 & \text{if } ADRR > x \ \& \ LBGI > y \\ 0 & \text{otherwise} \end{cases}$$

Where x and y are predefined values.

37. The method of claim 1, wherein SMBG data obtained from said patient is an individual SMBG reading.

38. The method of claim 1, wherein SMBG data obtained from said patient is all SMBG data collected from a patient in a predetermined cycle.

39. The system of claim 19, wherein SMBG data obtained from said patient is an individual SMBG reading.

40. The system of claim 19, wherein SMBG data obtained from said patient is all SMBG data collected from a patient in a predetermined cycle.

41. A computer program product comprising a non-transitory computer-readable storage medium containing computer-executable instructions for maintaining the health of a diabetic patient by preventing the occurrence of a hypoglycemic event in said patient, said instructions causing a computer to:
  obtain self monitoring blood glucose (SMBG) readings from the patient;
  measure glycemic variability of said patient and low blood glucose (BG) of said patient based on said obtained SMBG readings;
  create a bivariate distribution in said storage medium, which maps probability for an upcoming hypoglycemic event in said patient jointly to values of said measured glycemic variability and said measured low blood glucose (BG), wherein said bivariate distribution allows prediction of a predetermined percentage of hypoglycemic events below a predetermined BG value occurring within a predetermined future time period;
  optimize said bivariate distribution and track the optimized distribution over time using routine SMBG readings received from the patient;
  output a message to said patient when said optimized distribution indicates a certain probability for the occurrence of a hypoglycemic event in said patient within said predetermined future time period, based on SMBG data obtained from said patient; and
  cause said patient in response to receiving said message to take a physical action to prevent a hypoglycemic event from occurring in said patient.

42. The computer program product of claim 41, wherein SMBG data obtained from said patient is an individual SMBG reading.

43. The computer program product of claim 41, wherein SMBG data obtained from said patient is all SMBG data collected from a patient in a predetermined cycle.

* * * * *

UNITED STATES PATENT AND TRADEMARK OFFICE
CERTIFICATE OF CORRECTION

PATENT NO. : 10,431,342 B2
APPLICATION NO. : 13/394091
DATED : October 1, 2019
INVENTOR(S) : Boris P. Kovatchev and Marc D. Breton It is certified that error appears in the above-identified patent and that said Letters Patent is hereby corrected as shown below:

In the Specification

Column 1, Lines 8-11, please replace "Work described herein was supported by Federal Grant No. R01 DK51562, awarded by National Institutes of Health (NIH). The US Government has certain rights in the invention." with -- This invention was made with government support under Grant No. DK051562 awarded by the National Institutes of Health. The government has certain rights in the invention. --

Signed and Sealed this
Seventh Day of April, 2020

Andrei Iancu
*Director of the United States Patent and Trademark Office*